(12) United States Patent
Huelman et al.

(10) Patent No.: US 11,331,472 B2
(45) Date of Patent: *May 17, 2022

(54) DEVICES FOR DELIVERY OF ELECTRICAL CURRENT TO THE BODY AND RELATED METHODS FOR THERAPY

(71) Applicant: The Board of Trustees of the Leland Stanford Junior University, Stanford, CA (US)

(72) Inventors: Justin H. Huelman, Palo Alto, CA (US); Véronique Paule-Alberte D Peiffer, Sint-Truiden (BE)

(73) Assignee: The Board of Trustees of the Leland Stanford Junior University, Stanford, CA (US)

(*) Notice: Subject to any disclaimer, the term of this patent is extended or adjusted under 35 U.S.C. 154(b) by 149 days.

This patent is subject to a terminal disclaimer.

(21) Appl. No.: 16/543,453

(22) Filed: Aug. 16, 2019

(65) Prior Publication Data

US 2019/0374768 A1    Dec. 12, 2019

Related U.S. Application Data

(63) Continuation of application No. 15/619,398, filed on Jun. 9, 2017, now Pat. No. 10,406,348.

(60) Provisional application No. 62/369,826, filed on Sep. 20, 2016, provisional application No. 62/347,625, filed on Jun. 9, 2016.

(51) Int. Cl.
*A61N 1/04* (2006.01)
*A61N 1/32* (2006.01)

(52) U.S. Cl.
CPC ......... *A61N 1/0484* (2013.01); *A61N 1/0428* (2013.01); *A61N 1/0432* (2013.01); *A61N 1/325* (2013.01)

(58) Field of Classification Search
None
See application file for complete search history.

(56) References Cited

U.S. PATENT DOCUMENTS

2010/0057147 A1* 3/2010 Fassih ................ A61N 1/0484
607/2

FOREIGN PATENT DOCUMENTS

| EP | 1400182 A1 | 3/2004 |
|---|---|---|
| KR | 200350353 Y1 | 5/2004 |
| WO | WO2015183690 A1 | 12/2015 |
| WO | WO2015183690 A8 | 12/2015 |

* cited by examiner

*Primary Examiner* — Michael W Kahelin
*Assistant Examiner* — Elizabeth K So
(74) *Attorney, Agent, or Firm* — Lumen Patent Firm

(57) ABSTRACT

A device for delivery of electrical current to an area of the skin includes a first pad shaped in the form of a base having four finger-shaped protrusions; a second pad shaped in the form of a palm having a single thumb-shaped protrusion, where the first pad and the second pad each comprises a conductive layer and preferably has tabs on the edges; a first electrical connection system electrically connected to the conductive layer of the first pad; a second electrical connection system electrically connected to the conductive layer of the second pad; a controller circuit connected to the first electrical connection system and second electrical connection system; and a wearable power source. Alternatively, the device may also have the shape of a foot or other body part.

10 Claims, 28 Drawing Sheets

FIG. 4A
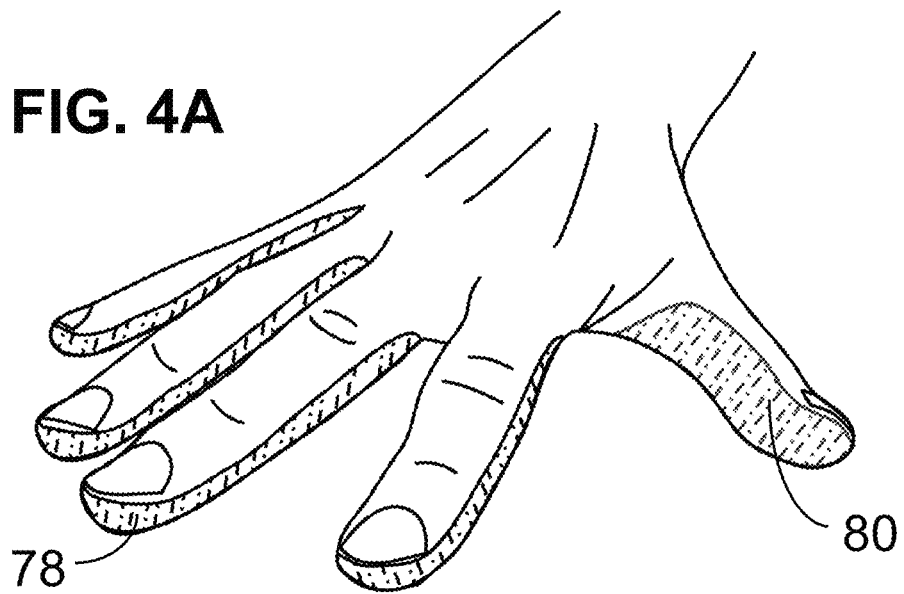
78  80
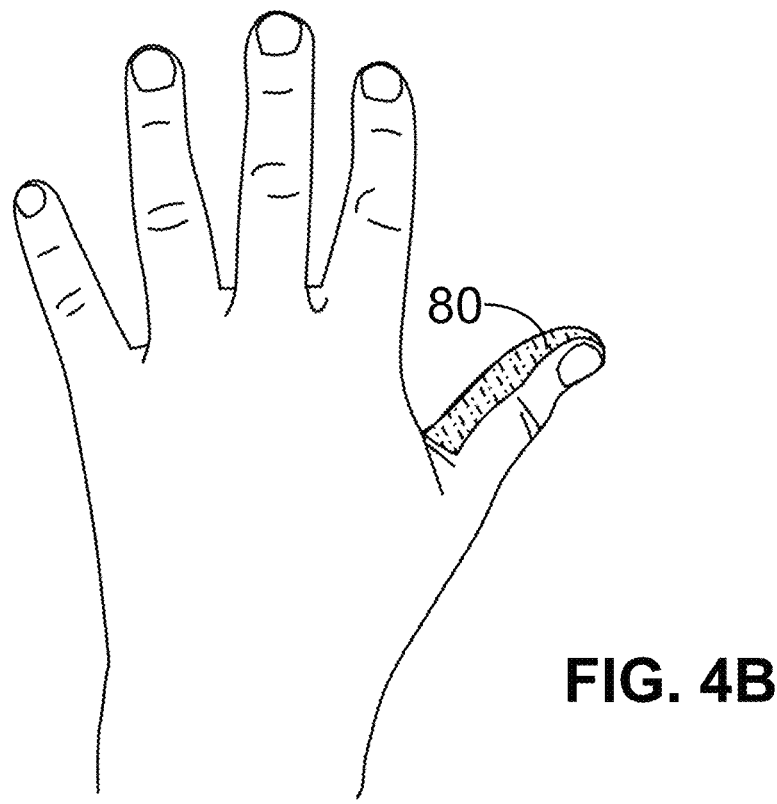
80
FIG. 4B

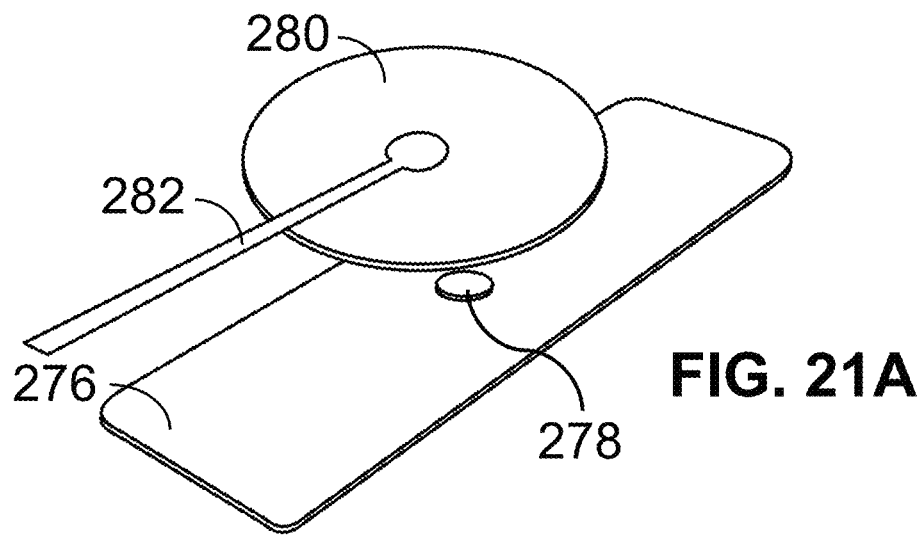
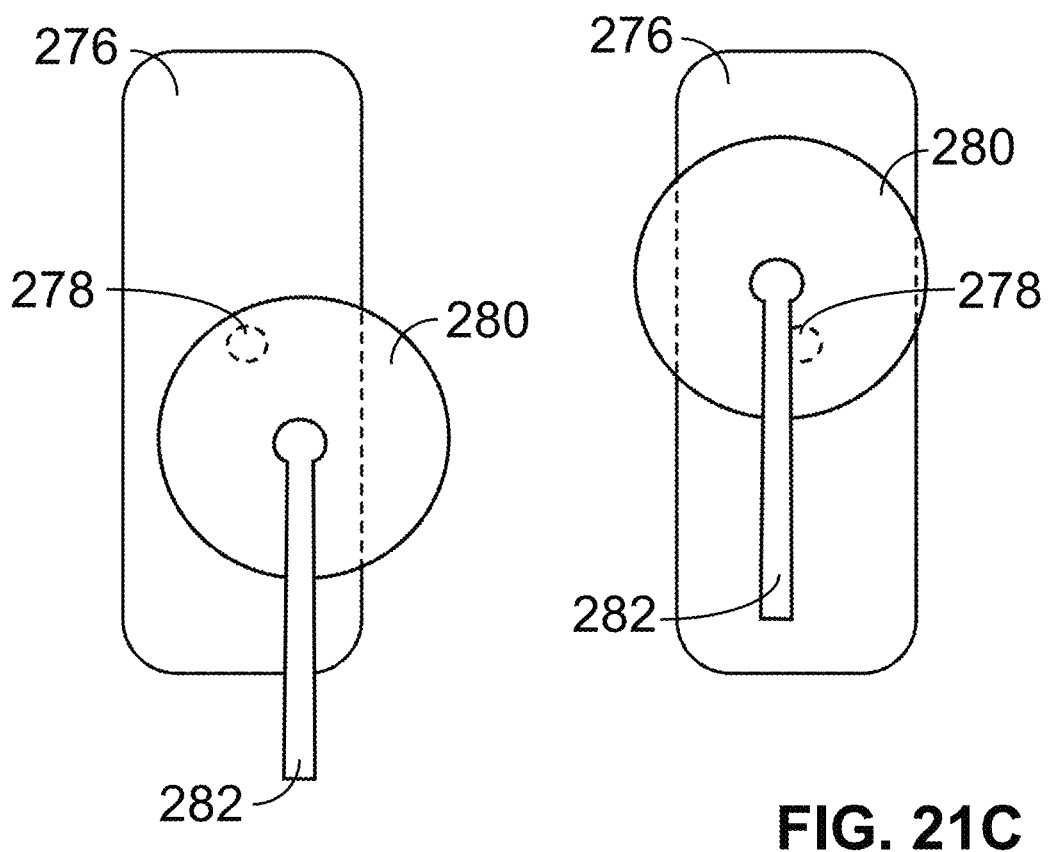
FIG. 21A
FIG. 21B
FIG. 21C

DEVICES FOR DELIVERY OF ELECTRICAL CURRENT TO THE BODY AND RELATED METHODS FOR THERAPY

CROSS-REFERENCE TO RELATED APPLICATIONS

This application is a continuation of U.S. patent application Ser. No. 15/619,398 filed Jun. 9, 2017, now U.S. patent Ser. No. 10/406,348, which claims priority from U.S. Provisional Patent Application 62/347,625 filed Jun. 9, 2016 and from U.S. Provisional Patent Application 62/396,826 filed Sep. 20, 2016, all of which are incorporated herein by reference.

STATEMENT REGARDING FEDERALLY SPONSORED RESEARCH OR DEVELOPMENT

None.

FIELD OF THE INVENTION

This disclosure relates generally to devices, systems and methods for delivery of electrical current to the body or body parts, and more particularly to iontophoresis devices for delivery of electrical current to the skin and their use in the management of hidrosis or treatment of hyperhidrosis.

BACKGROUND OF THE INVENTION

Iontophoresis is a well-known technique to introduce ions, electrons, or energy into the body, or to change or create an electric potential, or electrochemical gradients, using electrical current, or to transport ions across a membrane or into a tissue. It is a non-invasive technique that has a number of applications, including transdermal drug delivery to a pre-selected current delivery area, diagnosis of cystic fibrosis and treatment of excessive sweating, also known as hyperhidrosis, on a pre-selected current delivery area. Commercially available iontophoresis methods, devices and systems (that use water baths to conduct electricity to the body or body parts, e.g., the MD-2 Galvanic Iontophoresis Machine from RA Fischer, Calif.) can be inconvenient to use, for example, because they limit mobility during electrical current delivery, hence requiring a dedicated time commitment, and because they are messy to set up, may not ensure effective delivery to the entire pre-selected current delivery area, and/or can be uncomfortable for the user, for example because their use may induce bothersome tingling sensations, feeling of pins and needles, muscle tightening, erythema or mild or severe burns.

Developments aimed at making iontophoresis more convenient (e.g., those described in U.S. Pat. Nos. 8,150,525 and 7,643,874, the entirety of each which are hereby incorporated by reference herein) have not been commercialized, particularly for the purpose of treating hyperhidrosis. A key problem with these and other developments is that they do not provide effective ways to optimally conform to the pre-selected current delivery area. In particular, conductive garments make poor or intermittent contact with the body or body part, and such contact may lead to painful sensations and hence inconvenience. Poor contact or incomplete coverage of the pre-selected current delivery area may also lead to incomplete outcomes. For example, these technologies do not describe ways to cover a sufficient area of the sweat glands that sweat excessively on the body or targeted body part to adequately treat hyperhidrosis (excessive sweating) using electrical current, for example the sides of the fingers for palmar hyperhidrosis, and the sides of the feet for plantar hyperhidrosis. Additionally, these technologies do not describe ways to minimally or not treat parts that do not require management or treatment, for example the arms and knuckles in the case of palmar hyperhidrosis. These technologies also suffer from problems with manufacturability. For example, the garment described in U.S. Pat. No. 8,150,525 would be difficult to manufacture with simple techniques such as die-cutting tools.

Particularly for the management of hidrosis or treatment of hyperhidrosis the lack of a better solution presents a significant unmet clinical need, as no good management or treatment options exist for this population. Hyperhidrosis is caused by overactivity of the sympathetic nervous system that results in a dramatically increased sweat production, far beyond what is required for thermal regulation. People who are not familiar with the condition may not appreciate that hyperhidrosis is the dermatologic condition with the most dramatic impact on quality of life, worse than dermatitis, eczema and psoriasis. 75% of sufferers report that the condition affects their emotional health and the prevalence of depression is tripled in this population. The condition can be particularly debilitating during times in life where social interactions are crucially important. The youngest sufferers get bullied at school when required to hold hands, or are embarrassed when they hand in to their teacher paperwork soaked by perspiration. The condition is also particularly debilitating for adolescents: it affects them emotionally, for example feeling embarrassed when holding hands with someone. Sweaty hands also add pressure during job interviews, with more than 50% of adult patients reporting that the condition has negatively affected them in their professional career. Hidrosis (sweating) that does not reach the medical level of severity may be similarly bothersome to some individuals.

Current treatment options for hyperhidrosis each have at least one major drawback. Antiperspirants are prescribed as first-line treatment, but they are typically ineffective. Botulinum toxin injections can be used, but they are painful and expensive. Systemic medications, such as anticholinergics, are greatly limited by their adverse effects. Sympathetic (thoracic) surgery is an effective but invasive treatment that carries a significant risk of developing compensatory sweating in other body areas such as the chest and back. For the management of hidrosis any of these options would be cumbersome, invasive or expensive.

Thus, there remains a considerable need for methods, devices and systems to deliver electrical current to the body, skin, membrane or other tissue, that are convenient in use, that ensure effective delivery to a pre-selected current delivery area, result in minimal discomfort for the user, and/or are easy to manufacture, even at scale.

BRIEF SUMMARY OF THE INVENTION

In one aspect, the invention provides a device for delivery of electrical current to an area of skin. The device includes a first electrode assembly; a second electrode assembly; and a generator and controller system electrically connected to the first electrode assembly and the second electrode assembly. The generator and controller system is adapted to deliver an electrical current to the first electrode assembly and second electrode assembly. In addition, the first electrode assembly is a hand-shaped pad including one or more tabs on pad edges, an electrically conductive layer, and an adhesive hydrogel.

The second electrode assembly may be a hand-shaped pad comprising tabs on pad edges, an electrically conductive layer and an adhesive hydrogel. Either or both of the first electrode assembly and the second electrode assembly may have relief cuts. Each electrode assembly may also include an insulation layer and a bottom liner.

In another aspect, the invention provides a device for delivery of electrical current to an area of skin. The device includes a first set of one or more electrode assemblies serving as an anode, and first electrical connection system electrically connected to the first set of one or more electrode assemblies; a second set of one or more electrode assemblies serving as a cathode, and second electrical connection system electrically connected to the second set of one or more electrode assemblies; and a generator and controller system electrically connected to the first electrical connection system and the second electrical connection system. The generator and controller system includes a wearable power source and a controller circuit adapted to deliver electrical current to the first electrical connection system and second electrical connection system. Each electrode assembly of the first set of one or more electrode assemblies and the second set of one or more electrode assemblies is a pad comprising an electrically conductive layer and an adhesive hydrogel. The first set of one or more electrode assemblies and the second set of one or more electrode assemblies together form a hand-shaped pad. At least one electrode assembly of the first set of one or more electrode assemblies and the second set of one or more electrode assemblies comprise one or more tabs on pad edges.

At least one electrode assembly of the first set of one or more electrode assemblies and the second set of one or more electrode assemblies may have relief cuts. Each electrode assembly may include an insulation layer and a bottom liner.

In another aspect, the invention provides a device for delivery of electrical current to an area of skin. The device includes a first pad shaped in the form of a base having four finger-shaped protrusions; a second pad shaped in the form of a palm having a single thumb-shaped protrusion, where the first pad and the second pad each comprises a conductive layer; a first electrical connection system electrically connected to the conductive layer of the first pad; a second electrical connection system electrically connected to the conductive layer of the second pad; a controller circuit connected to the first electrical connection system and second electrical connection system; and a wearable power source.

The device may further include a compressive glove. The wearable power source may be attached to the backside of the compressive glove. At least one pad of the first pad and the second pad may have one or more tabs on pad edges. Preferably, the first pad is an anode and the second pad is a cathode. Preferably, an area of the first pad is equal to 33% to 300% an area of the second pad. The first pad and the second pad each may include an insulation layer, an adhesive hydrogel, and a bottom liner. The first pad and the second pad may be connected with a non-conductive material. The first pad or the second pad or both may have one or more relief cuts. Distal ends of adjacent finger-shaped protrusions of the four finger-shaped protrusions are preferably separated by a distance equal to 1.25 times a width of a narrower finger-shaped protrusion of the adjacent finger-shaped protrusions that excludes tabs on pad edges or more. An angle between a longitudinal axis of the single thumb-shaped protrusion and a longitudinal axis of one of the four finger-shaped protrusions that is adjacent to the single thumb-shaped protrusion is preferably at least 20°. A longitudinal axis of a distal section of the single thumb-shaped protrusion is preferably separated by a distance of 2 mm or more from a midpoint of the single thumb-shaped protrusion at a base of the single thumb-shaped protrusion. The controller circuit preferably includes instructions to limit a density of the electrical current below a selectable predetermined threshold.

BRIEF DESCRIPTION OF THE DRAWING FIGURES

These and other features, aspects and advantages of the various devices, systems and methods presented herein are described with reference to drawings of certain embodiments, which are intended to illustrate, but not to limit, such devices, systems and methods. It is to be understood that the attached drawings are for the purpose of illustrating concepts of the embodiments discussed herein and may not be to scale.

FIGS. 4A-B illustrate a right hand and a left hand, showing with shading the palmar side of each hand.

Figures 5A, 5B:
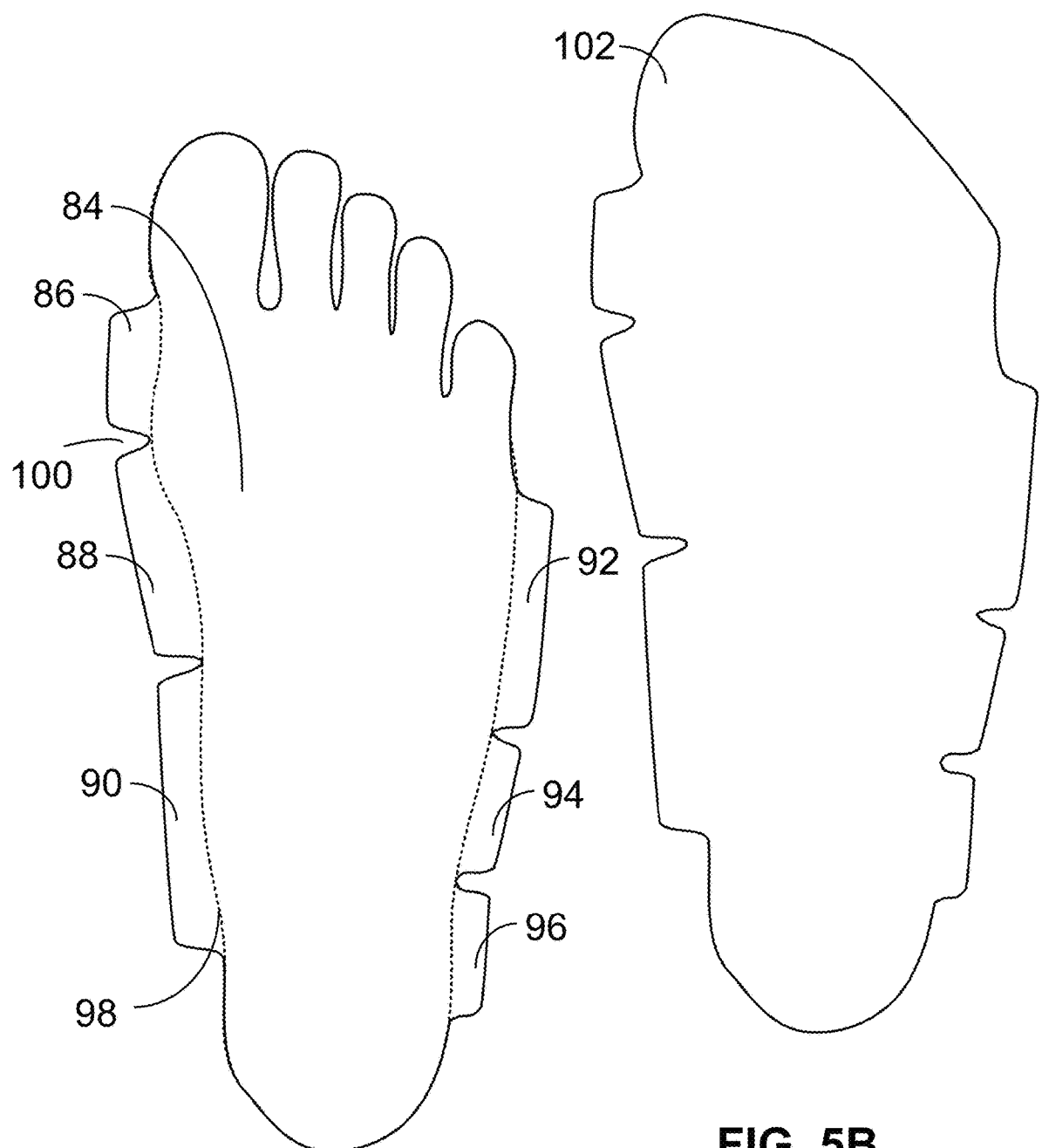

FIGS. 5A-B illustrate prints of electrode assemblies that cover the parts of a foot that contain eccrine sweat glands, according to two embodiments.

Figure 6A:
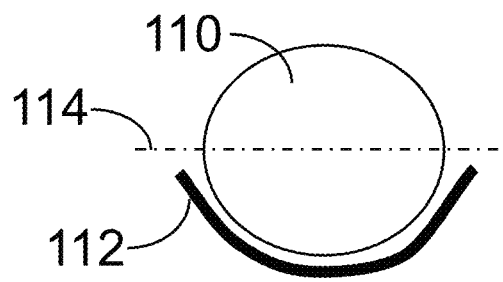
Figure 6B:
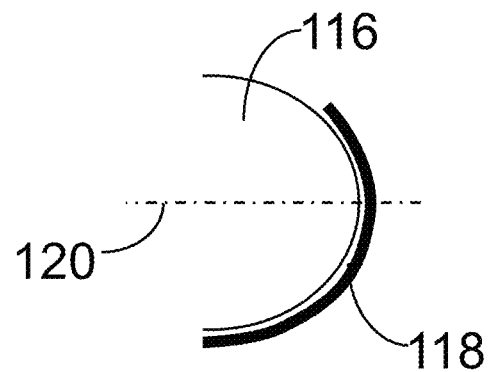

FIGS. 6A-B illustrate cross-sections of a finger and the side of a palm proximal to the little finger with electrode assembly, according to two embodiments.

Figure 7:
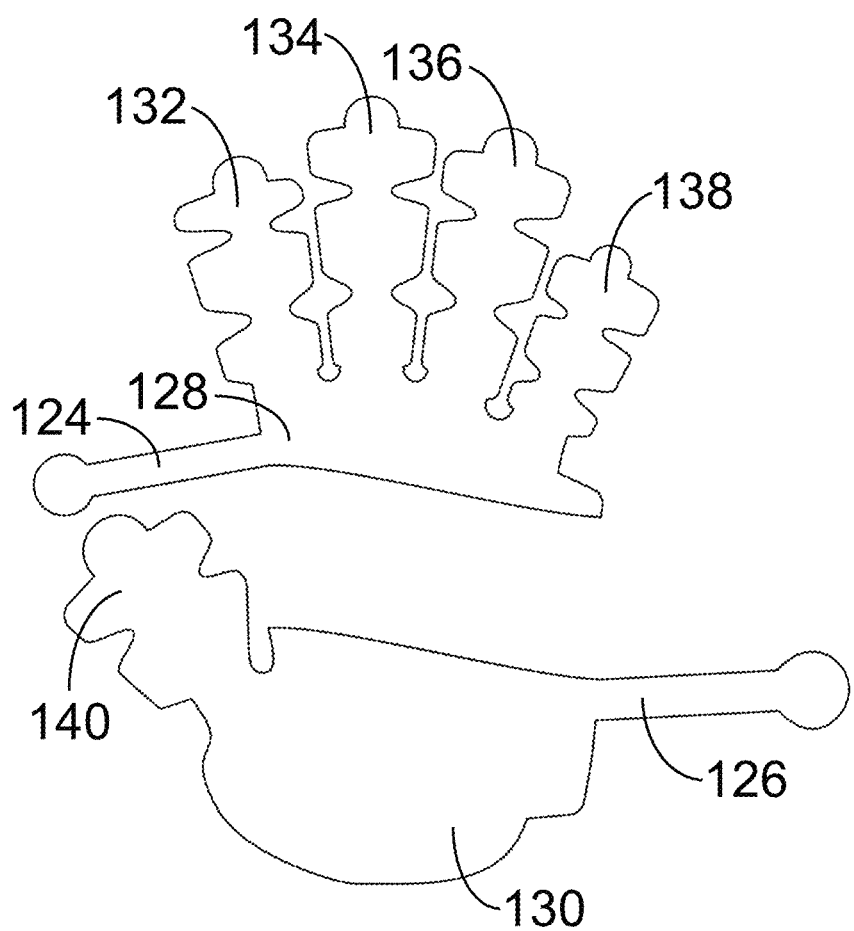

FIG. 7 illustrates the print of a set of two electrode assemblies with connecting protrusions for the hand, according to one embodiment.

Figure 8:
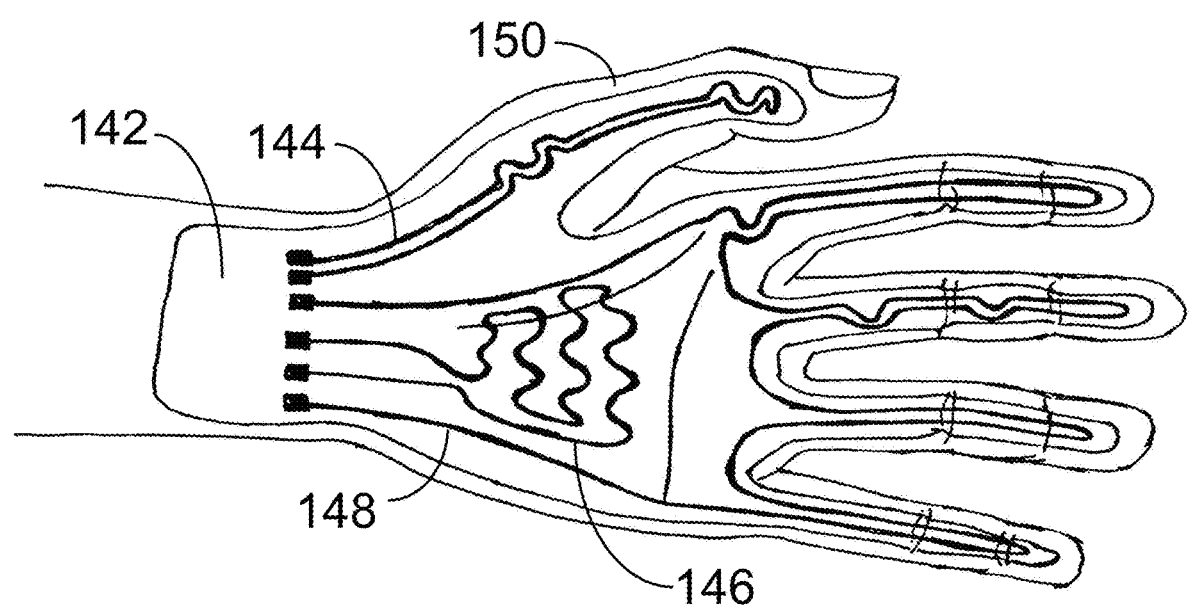

FIG. 8 illustrates an electrode assembly comprising a thin, flexible conductive film with electrically conductive traces on the palm and fingers of the hand, according to an embodiment.

Figure 9:
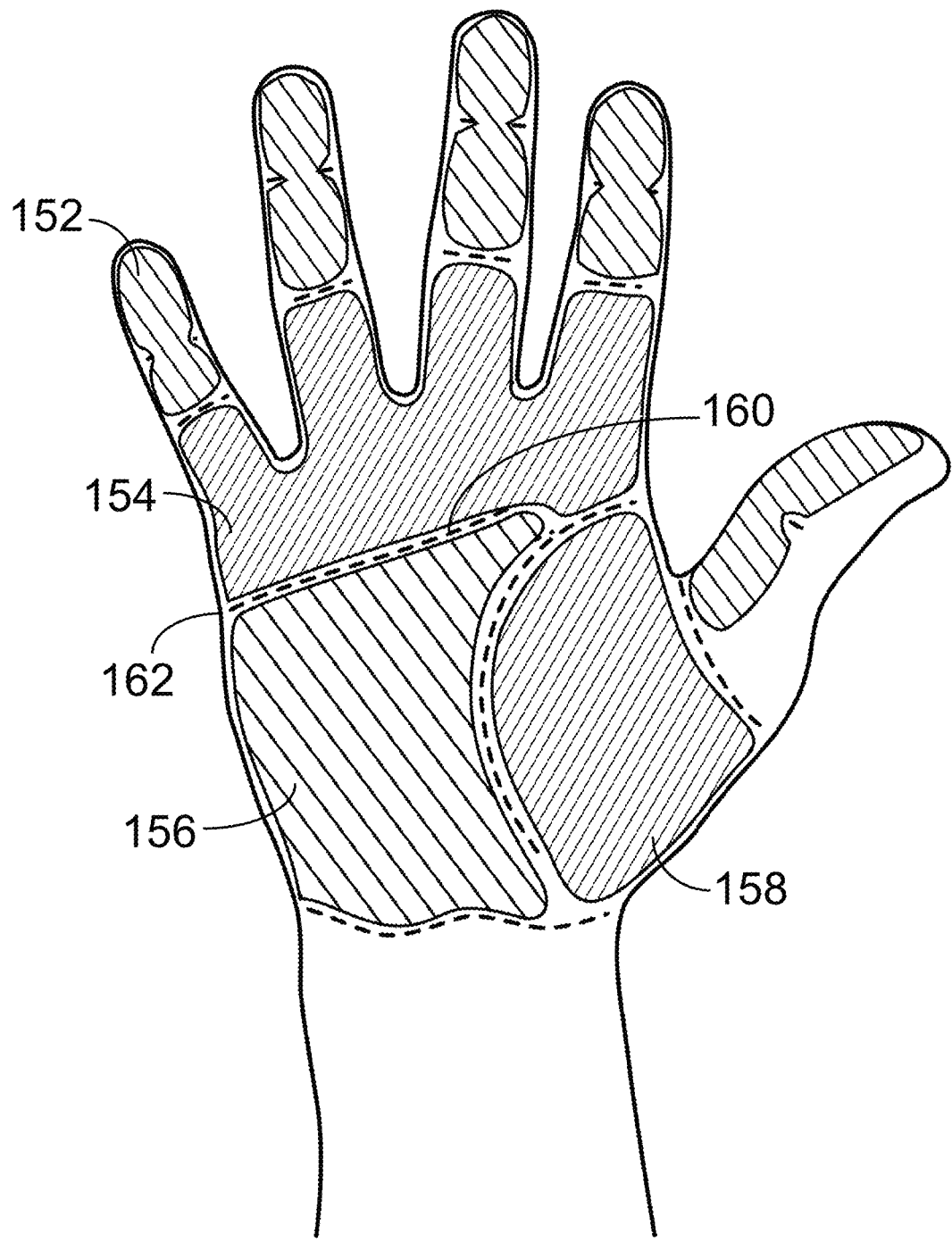

FIG. 9 illustrates a configuration of electrode assemblies that covers the parts of a hand that contain eccrine sweat glands and allows optimal hand movement, according to an embodiment.

Figure 10:
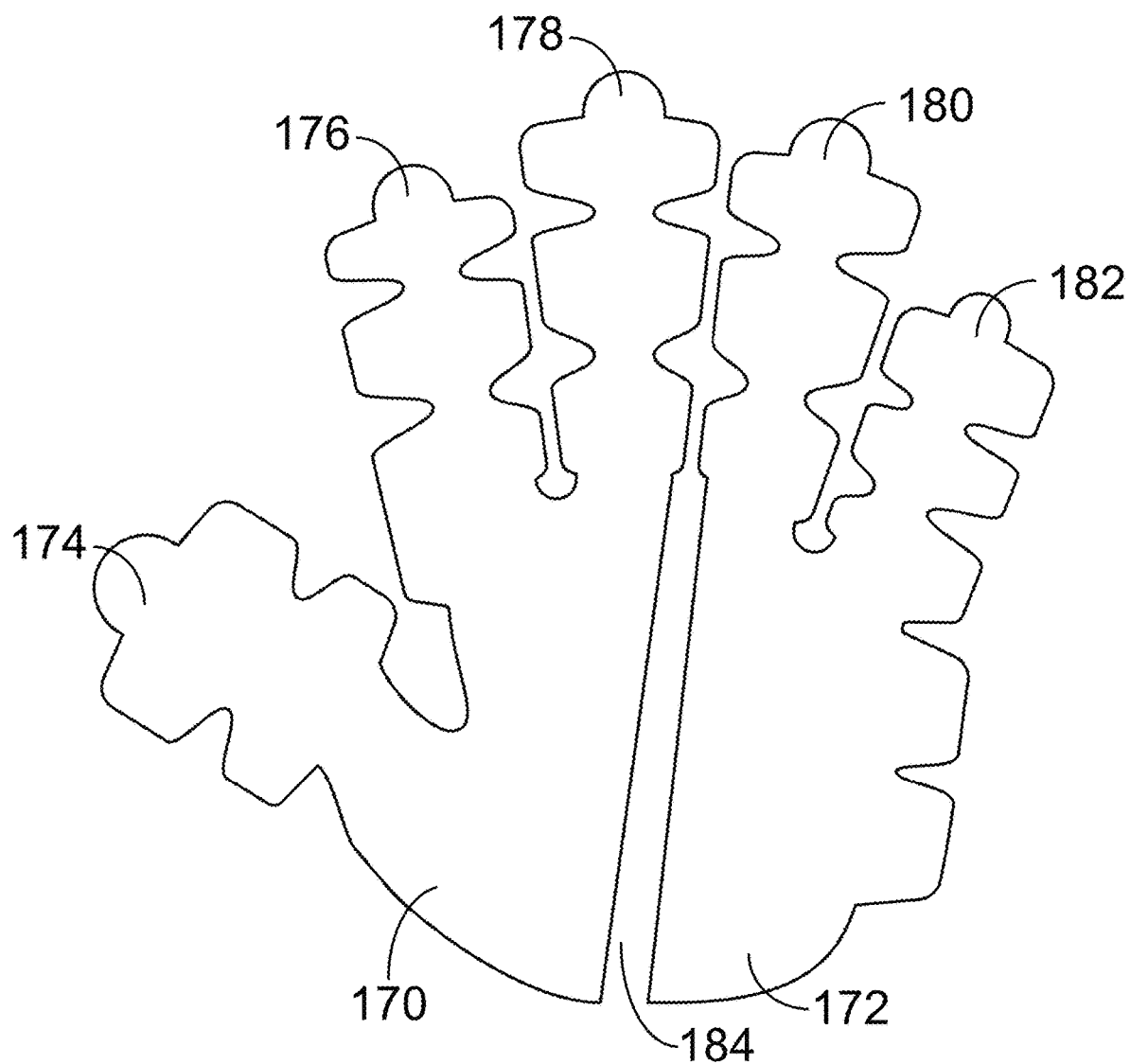

FIG. 10 illustrates the print of a set of two electrode assemblies that together cover the parts of a hand that contain eccrine sweat glands, according to an embodiment.

Figure 11:
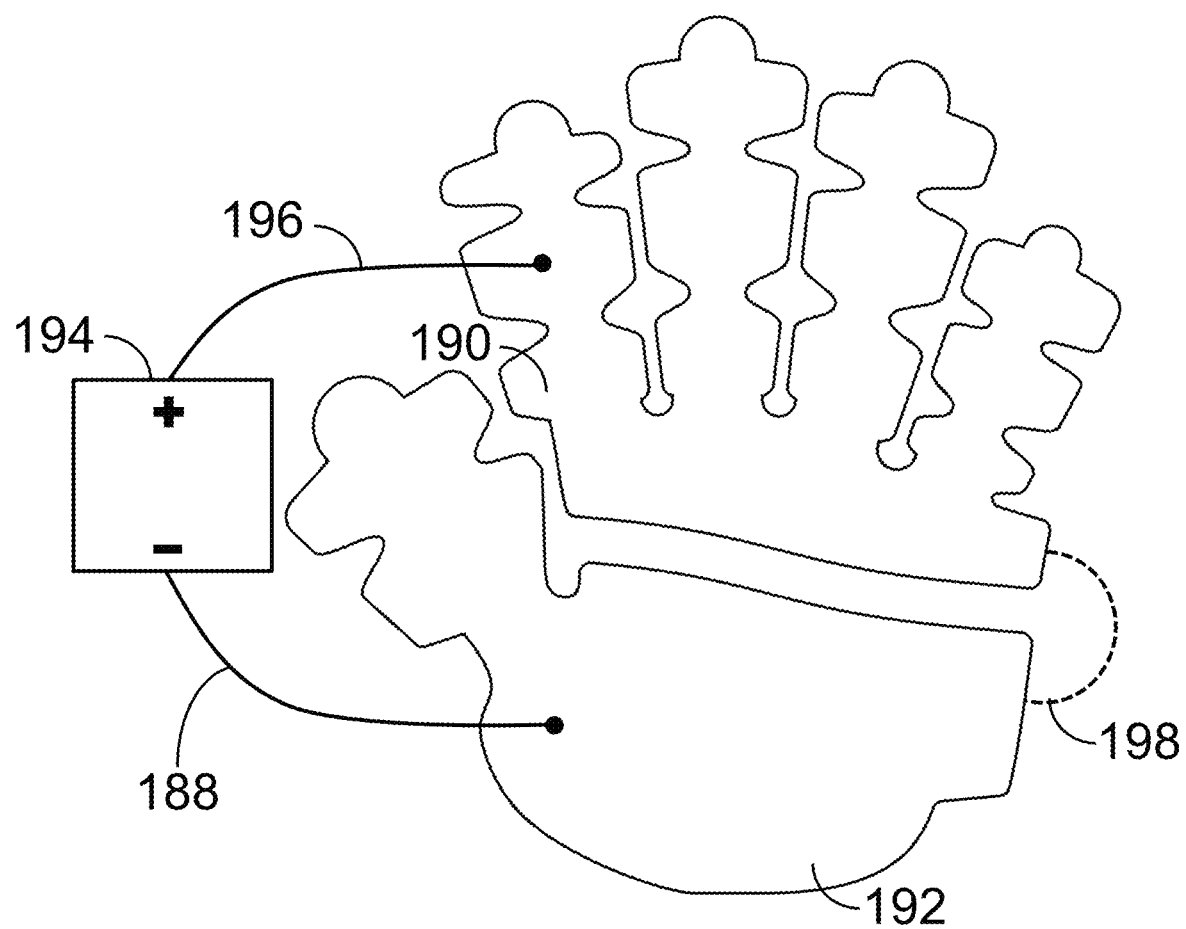

FIG. 11 illustrates the print of a set of two electrode assemblies that are connected to a power source and to a hand, according to an embodiment.

Figure 12B:
Figure 12A:

FIGS. 12A-B show an iodine imprint test for an untreated left hand and a treated right hand, after treatment with the set-up shown in FIG. 11.

Figure 13:
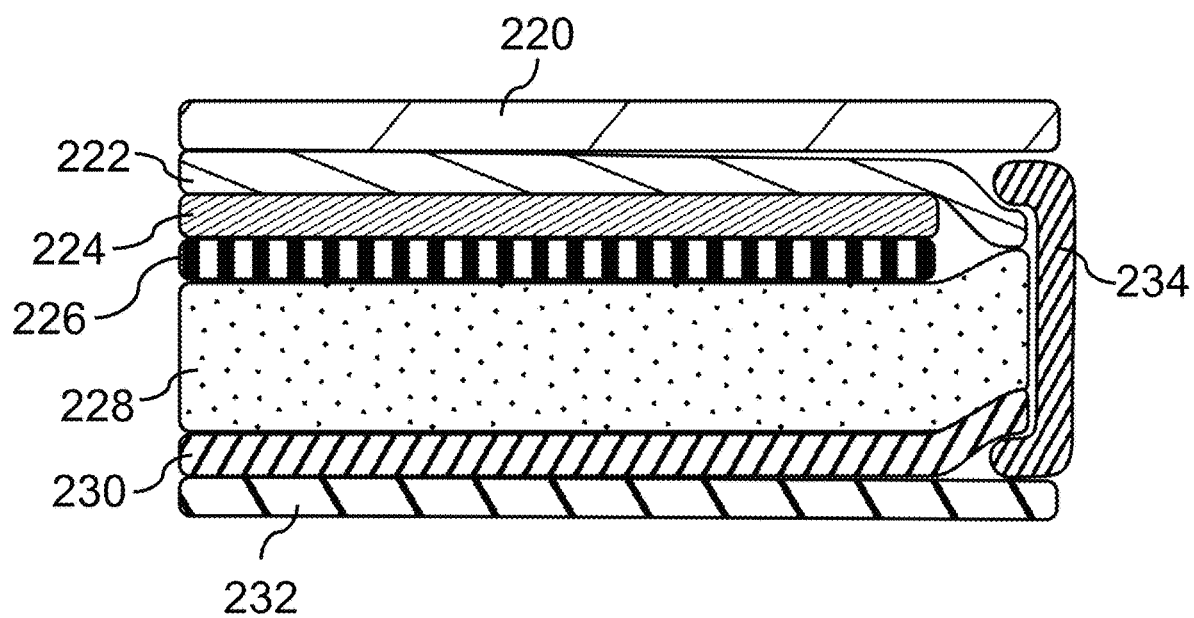

FIG. 13 illustrates an electrode assembly comprising a stabilizing liner, an insulation layer, a conductive layer, a fuse layer, a carrier, an adhesive, a bottom liner, and an edge protection according to an embodiment.

Figure 14:
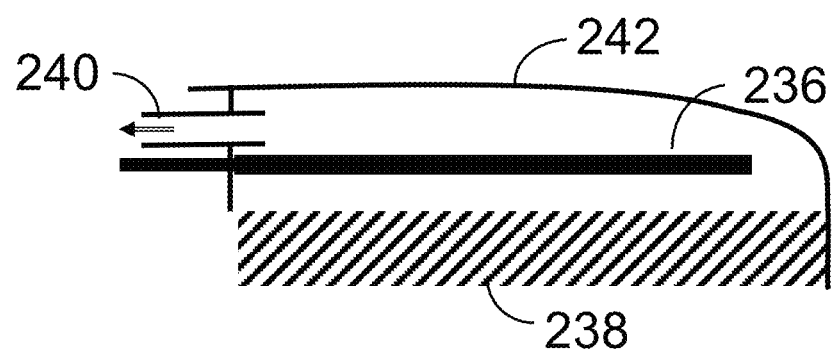

FIG. 14 illustrates an electrode assembly and a suction device according to an embodiment.

Figure 15:
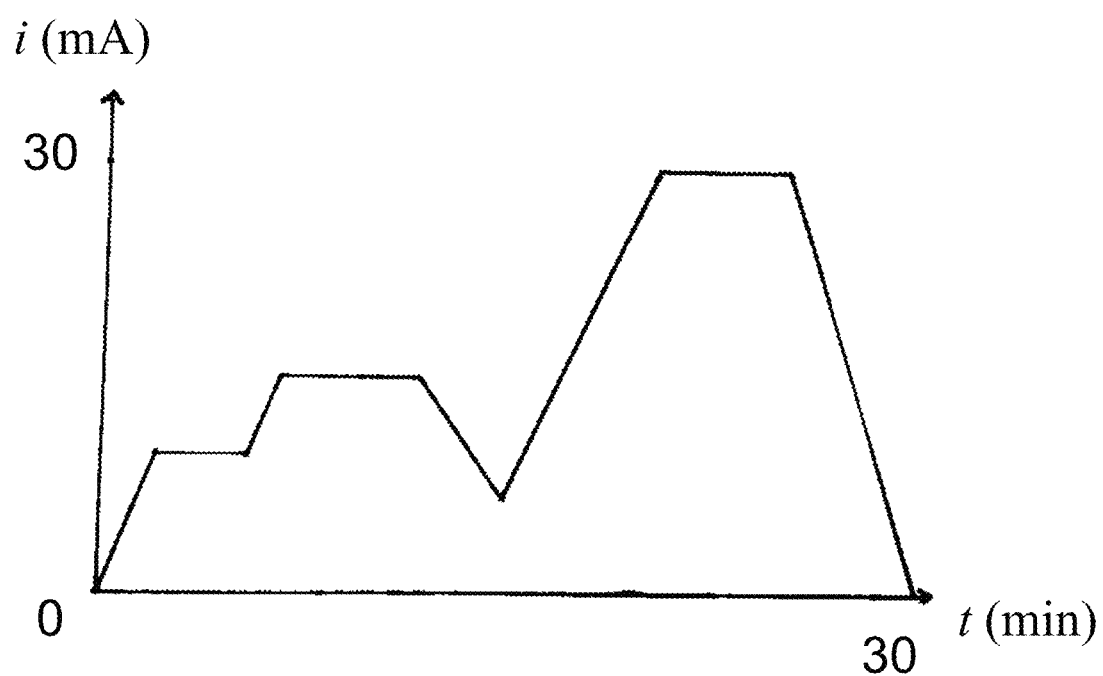

FIG. 15 illustrates an example electrical current profile over time, with direct current and stepwise changes in current, according to an embodiment of the invention.

Figure 16:
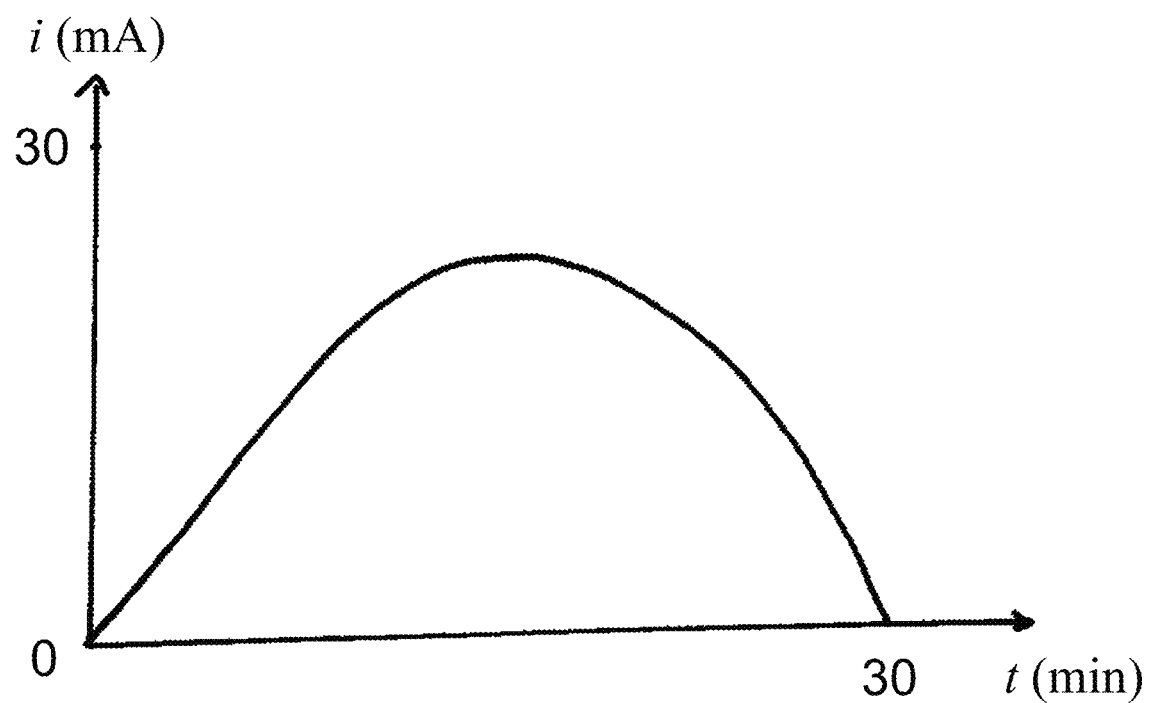

FIG. 16 illustrates an example electrical current profile over time, with direct current and continuous changes in current, according to an embodiment of the invention.

Figure 17:
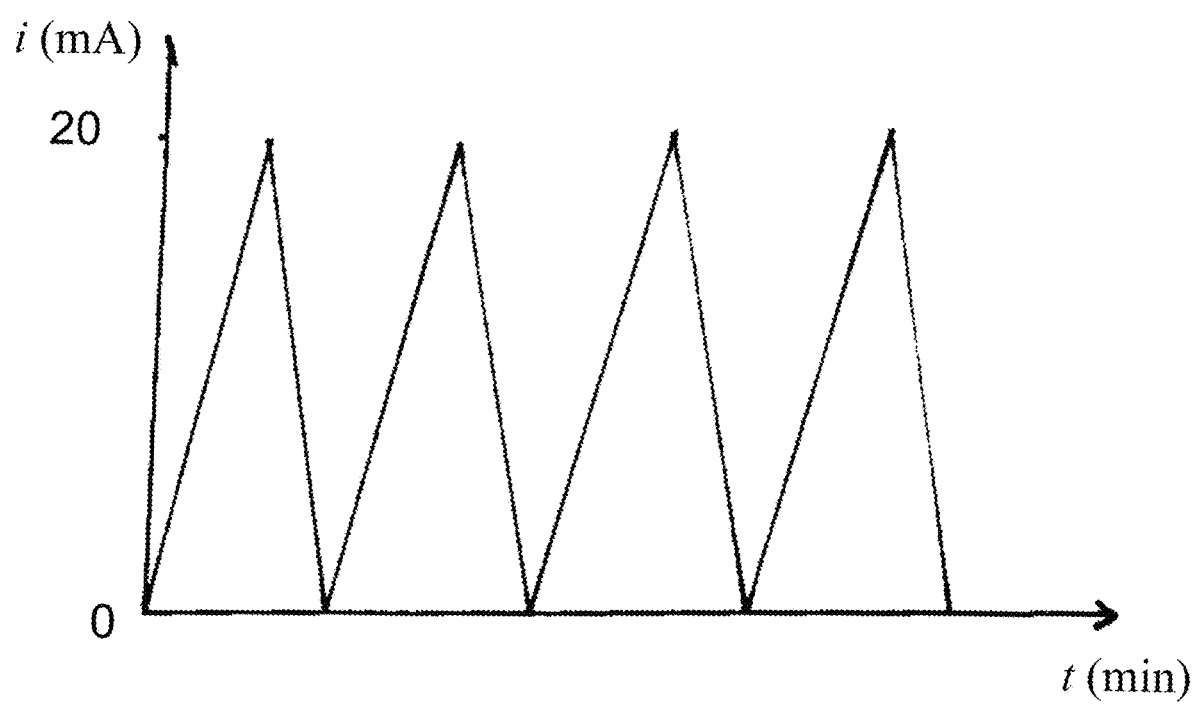

FIG. 17 illustrates an example electrical current profile over time, with alternating current and a direct current off-set, according to an embodiment of the invention.

Figure 18A:
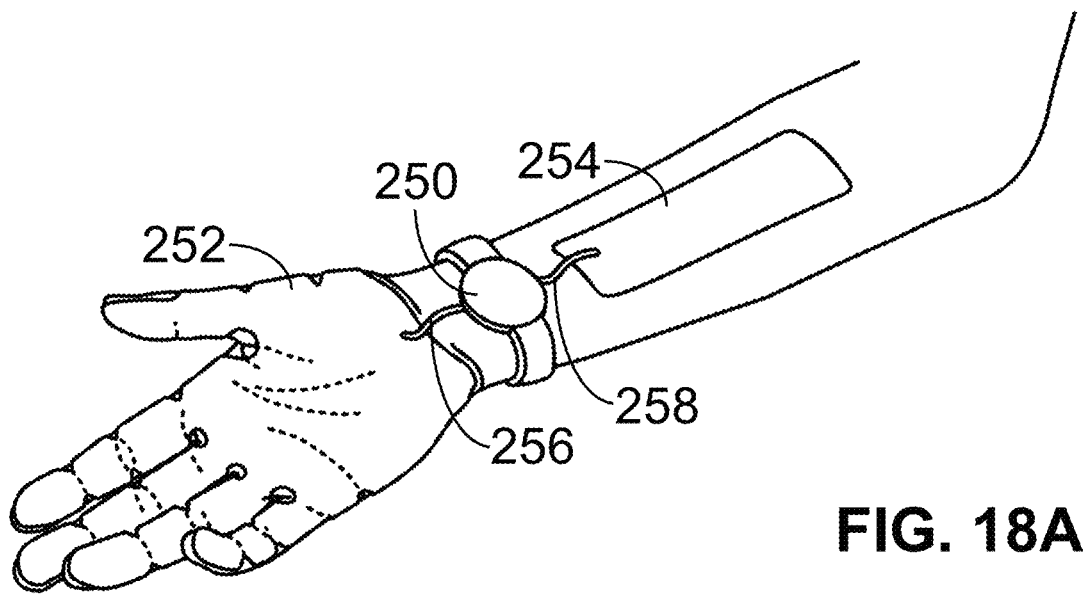
Figure 18B:
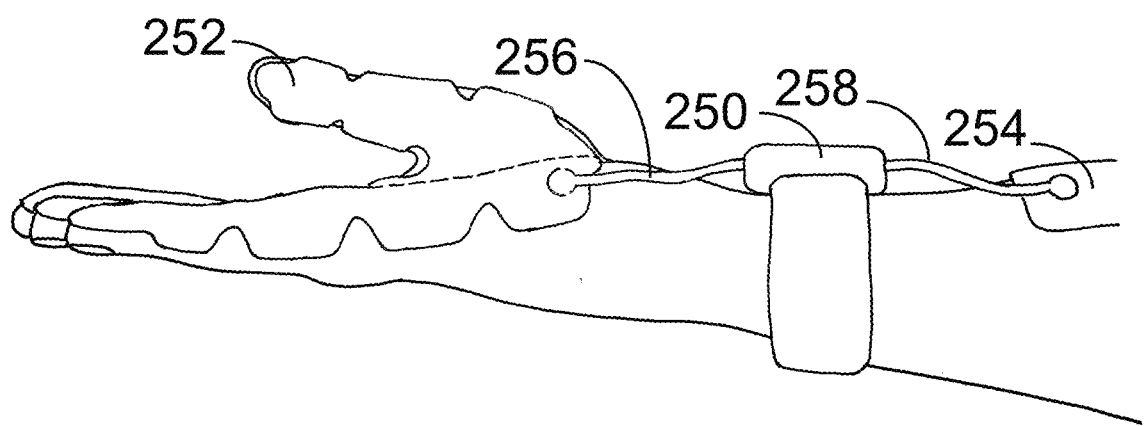

FIGS. 18A-B are two views of an iontophoresis device according to one embodiment, in which a generator and controller system is connected to a user's wrist, one electrode assembly is placed on the hand and another electrode assembly is placed on the forearm.

Figure 19:
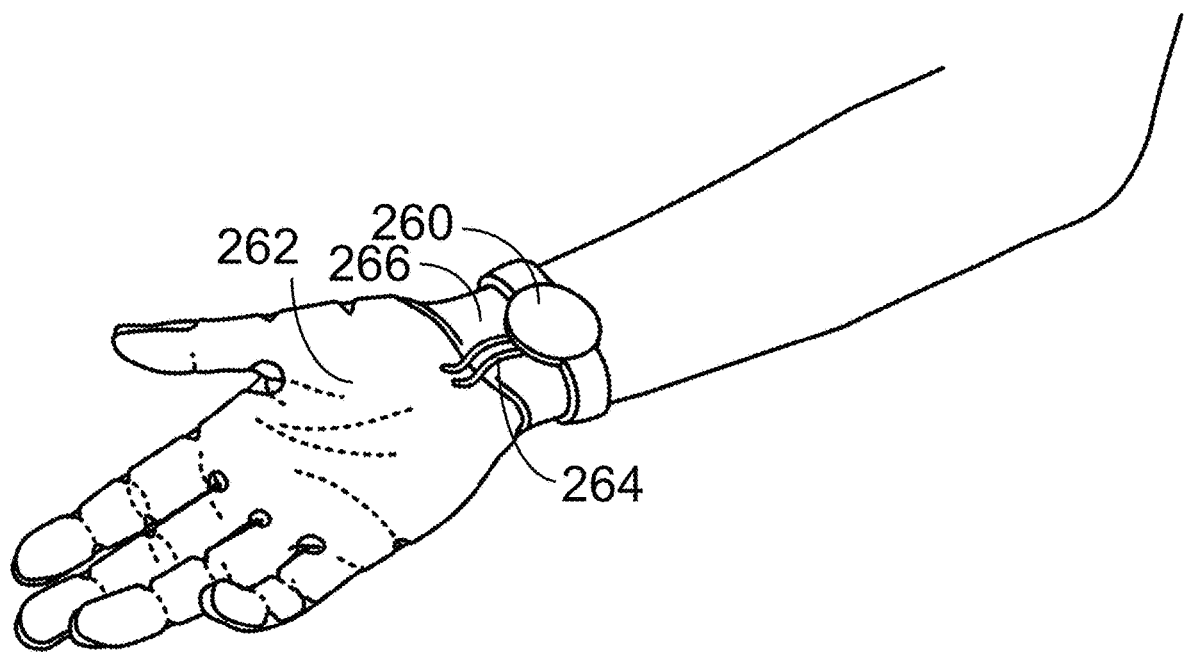

FIG. 19 illustrates an iontophoresis device according to an embodiment, in which a generator and controller system is connected to a user's wrist, and the electrode assemblies are placed on the hand.

Figure 20:
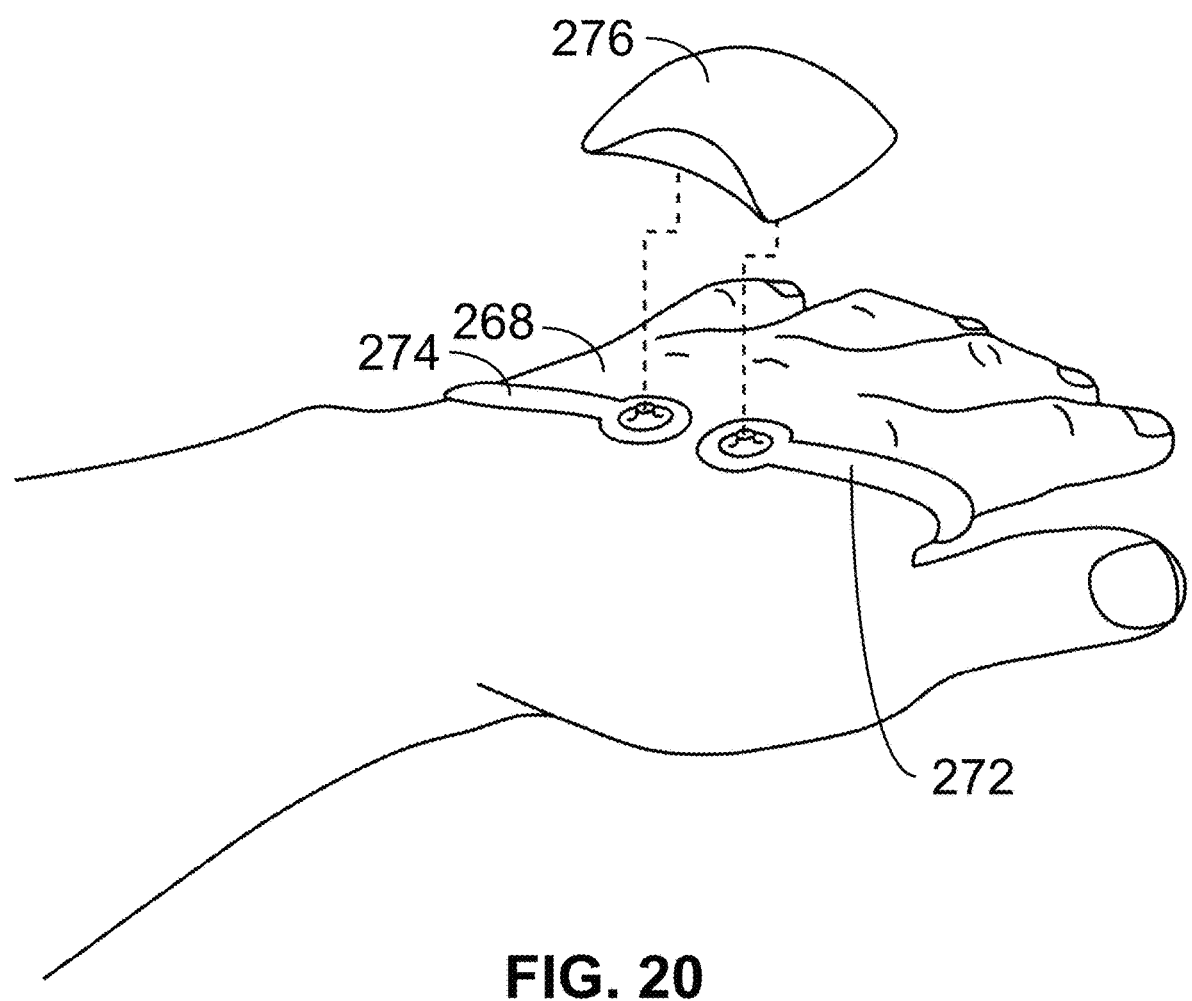

FIG. 20 illustrates a generator and controller system being connected to a hand with connecting protrusions, according to an embodiment of the invention.

FIGS. 21A-C are three views of conductive connectors or zones that electrically connect an electrode assembly to a generator and controller system, according to an embodiment of the invention.

Figure 22:
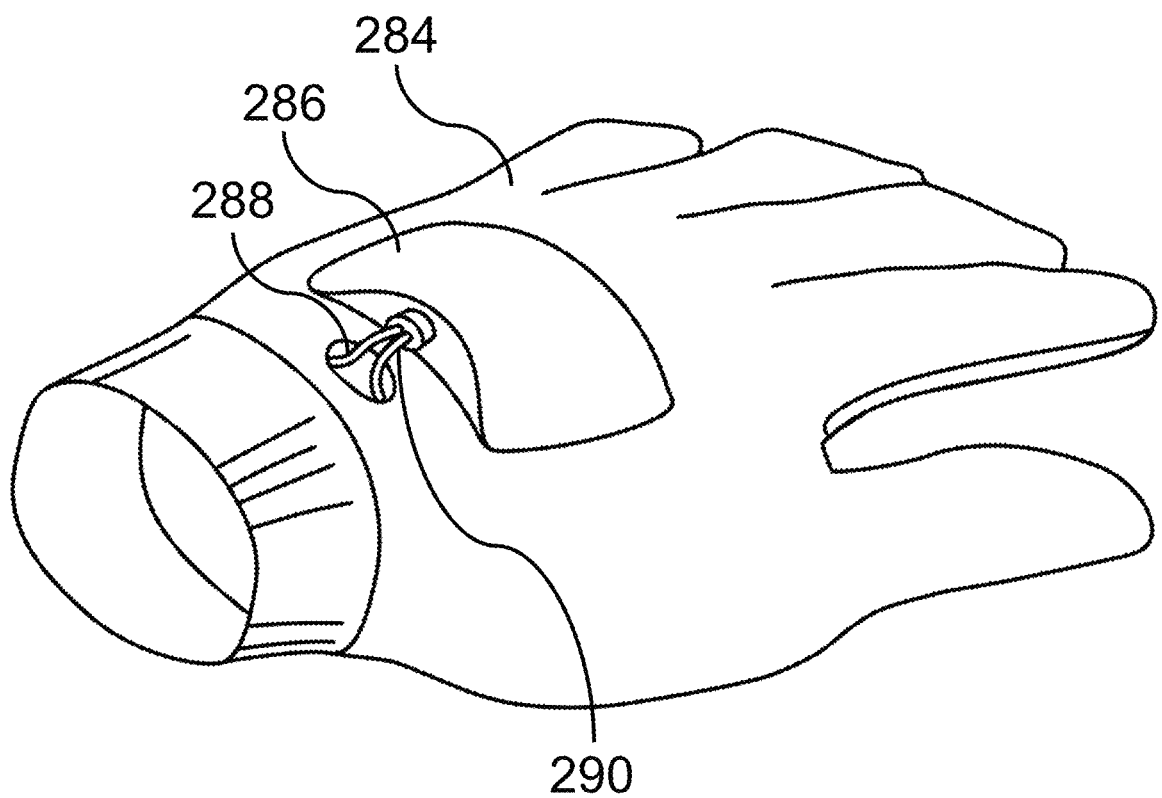

FIG. 22 illustrates a glove support system that is connected to a generator and controller system, where the generator and controller system is connected to the electrode assemblies through wiring, according to an embodiment.

Figure 23:
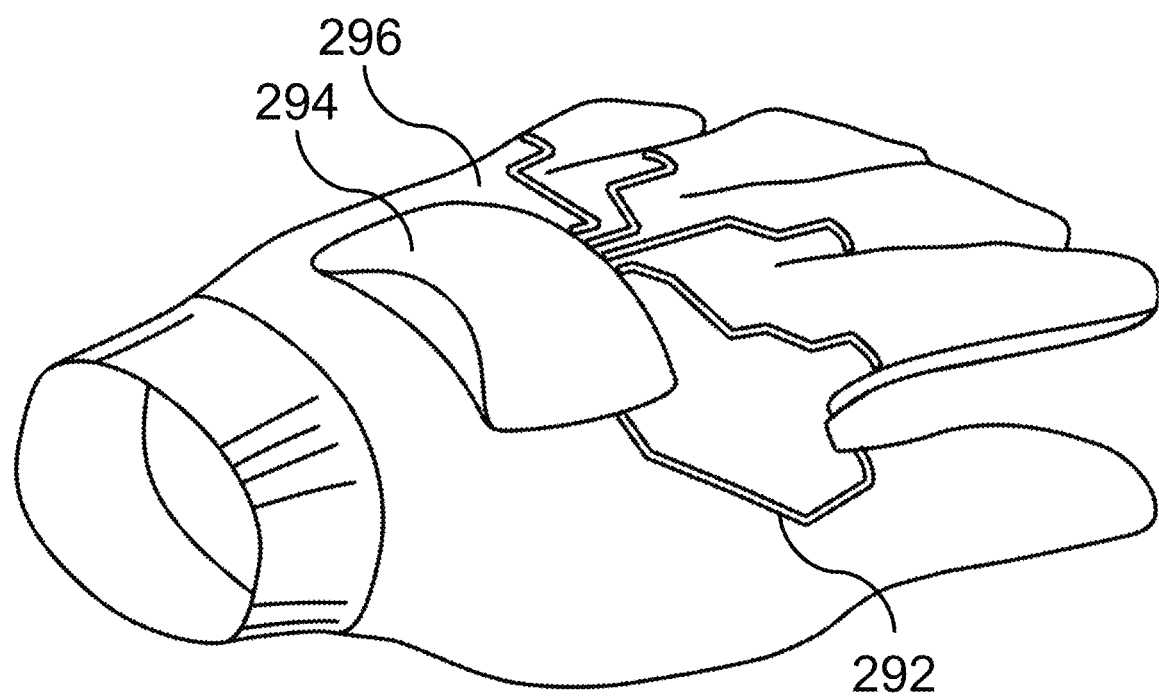

FIG. 23 illustrates a glove support system that is connected to a generator and controller system, where the connecting components are integrated into the glove support system, according to an embodiment.

Figure 24:
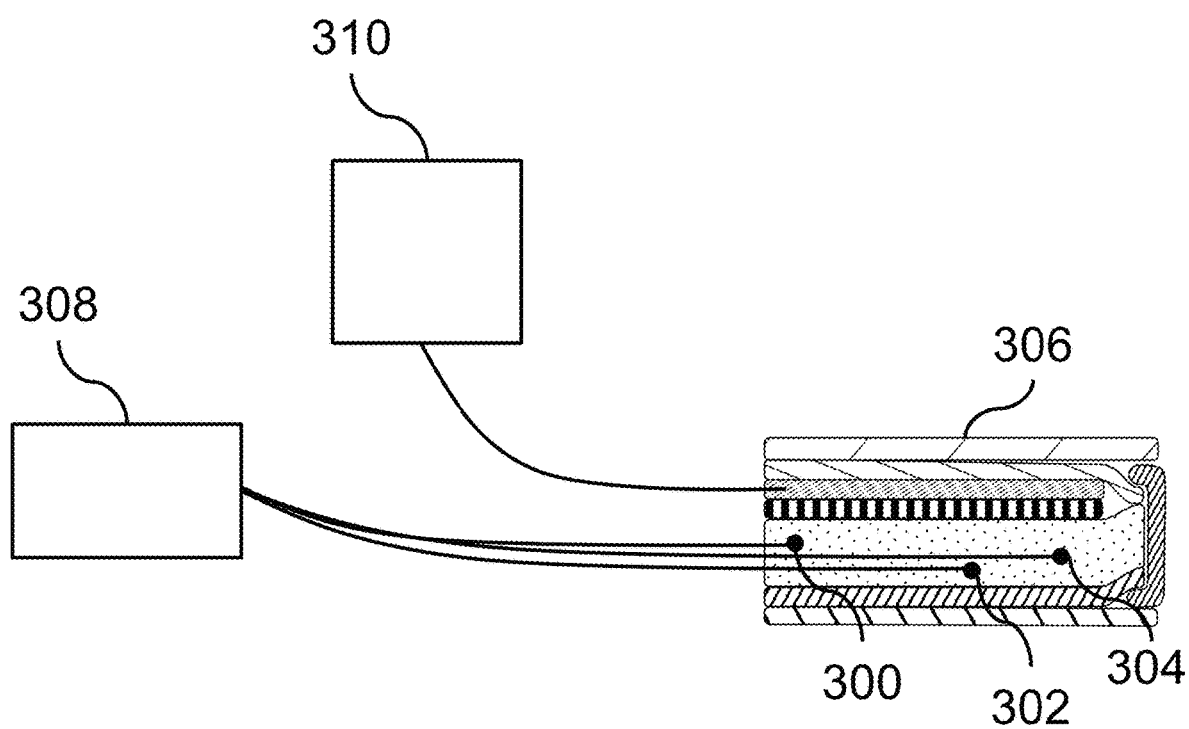

FIG. 24 illustrates an electrode assembly connected to a generator and controller system and a sensor system, according to an embodiment.

Figure 25:
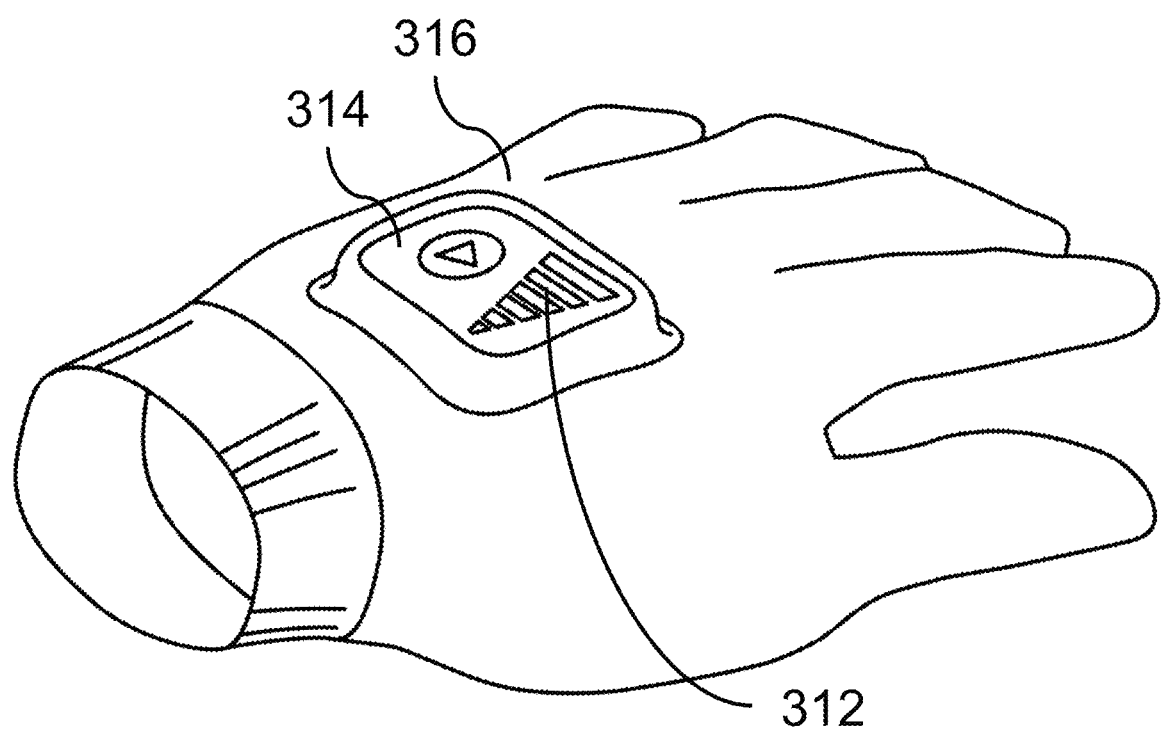

FIG. 25 illustrates a glove support system that is connected to a generator and controller system with a user interface, according to an embodiment.

Figure 26:
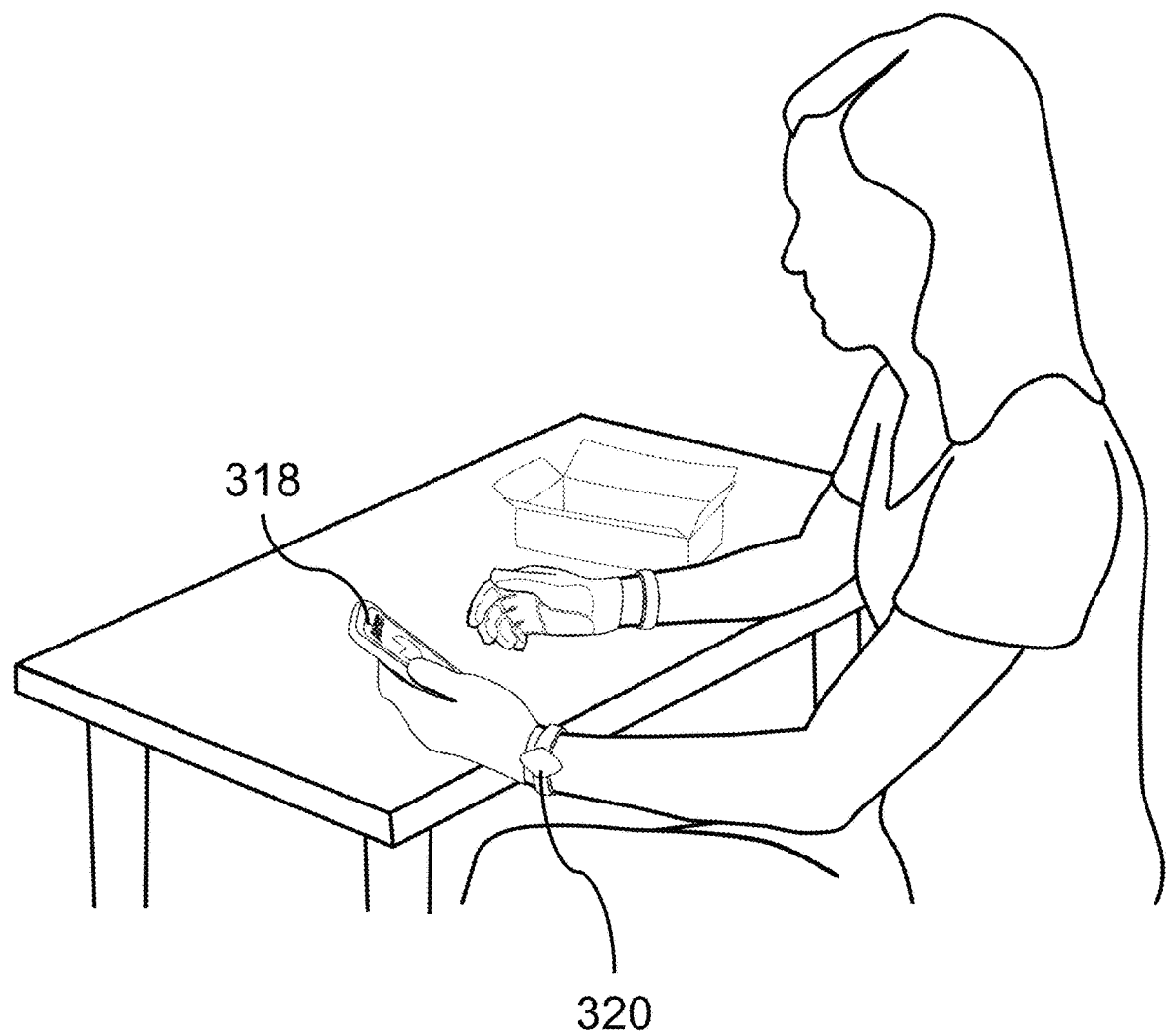

FIG. 26 illustrates a set-up for management of hidrosis or treatment of hyperhidrosis including a user-interfacing device, according to an embodiment.

Figure 27:
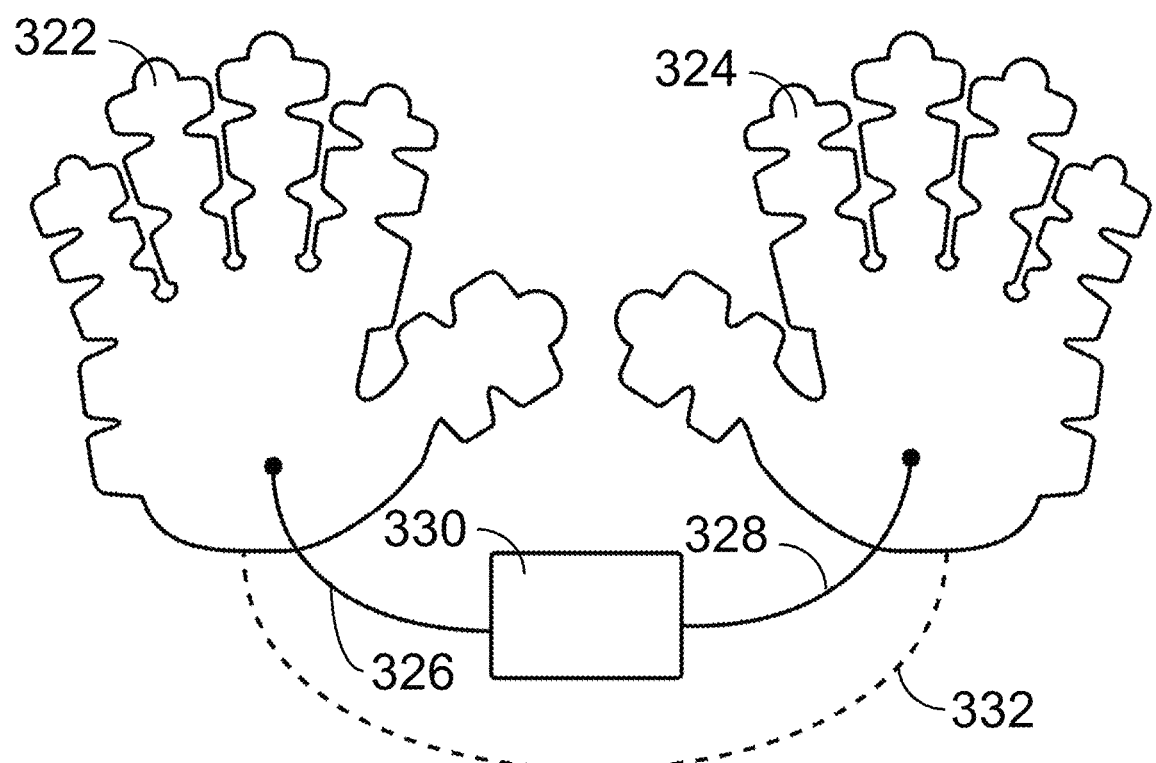

FIG. 27 illustrates two hand-shaped electrode assemblies connected to the hands and connected to a generator and controller system with wiring, according to an embodiment.

Figure 28:
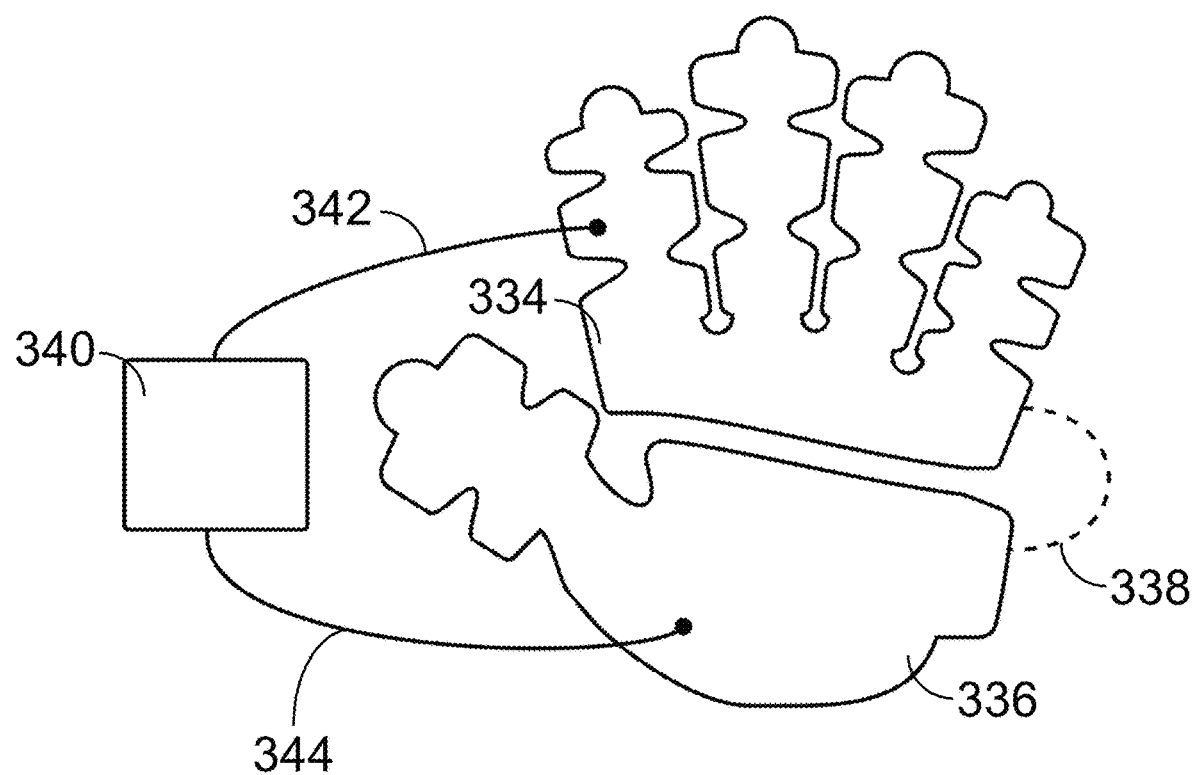

FIG. 28 illustrates the print of a set of two electrode assemblies that together cover the parts of a hand that contain eccrine sweat glands and that are connected to a power source and to a hand, according to an embodiment.

DETAILED DESCRIPTION OF THE INVENTION

Embodiments of the present application relate to methods, devices and systems for delivery of electrical current to the body. It is anticipated that many of these methods, devices and systems can be implemented either individually or in concert with one another. Furthermore, the modalities of electrical current delivery disclosed herein may be applicable to any place on the body where delivery of electrical current is desired, including the hand, palm, back of the hand, wrist, foot, sole, top of the foot, ankle, armpit, arm, leg, groin, face, neck, back or chest. For example, areas containing large numbers of skin appendages can be targeted such as eccrine glands, apocrine glands, apoeccrine glands, sebaceous glands, salivary glands, hair follicles or arrector pili muscles.

With reference to the drawings disclosed in this specification, the particulars shown are by way of example and for purposes of illustrative discussion of certain embodiments. In this regard, not all structural details may be shown in detail. Accordingly, it should be understood that the technology is not limited in its application to the details of construction and the arrangement of components set forth in the descriptions or illustrations provided herein.

Iontophoresis Device

Iontophoresis Device: Components Overview

Figure 1:
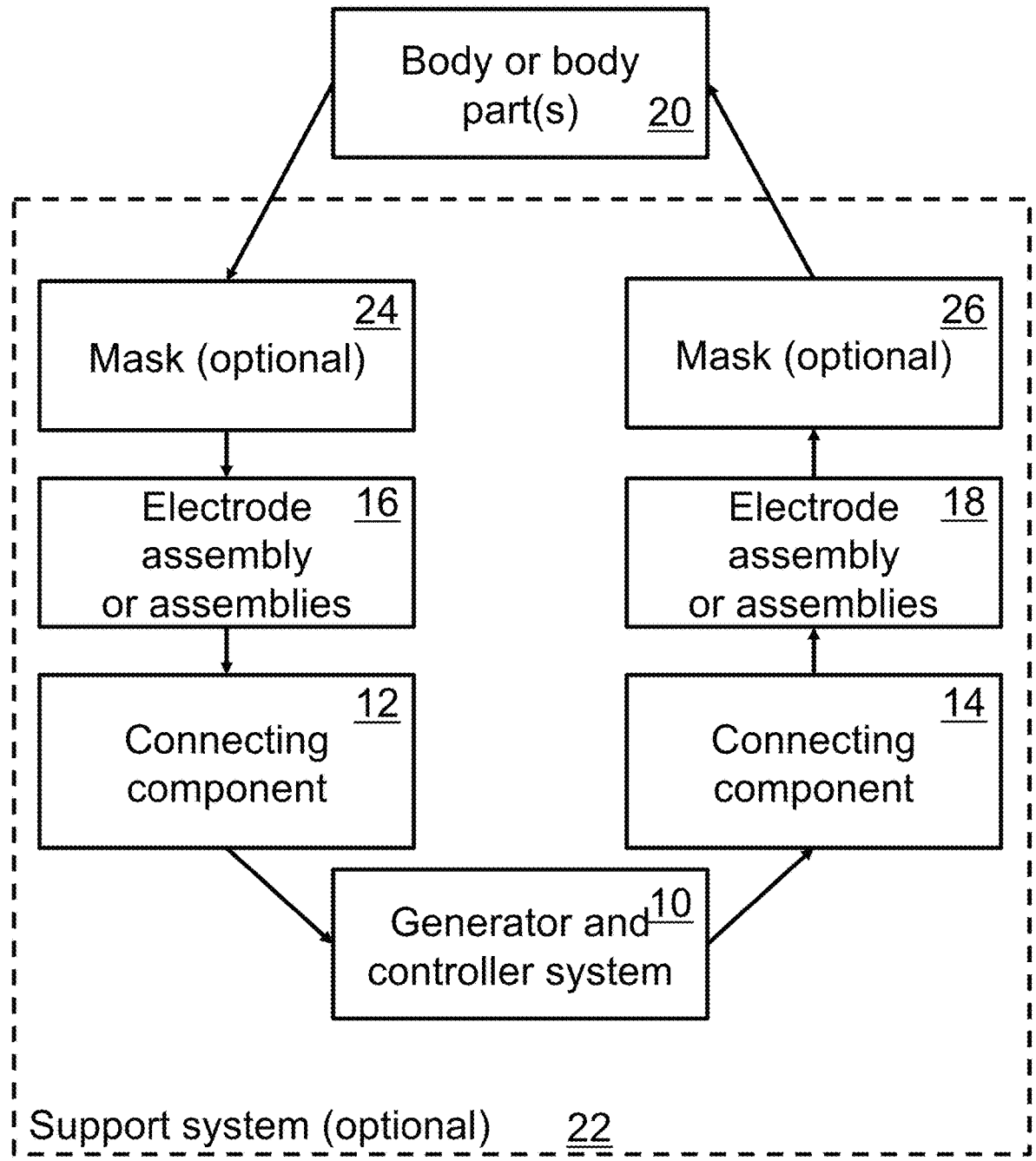
FIG. 1 is a schematic drawing of an iontophoresis device with electrode assemblies, connecting components, a generator and controller system, a body or body part(s), an optional support system and optional masks between the electrode assemblies and body or body parts, according to embodiments of the invention.

As illustrated in FIG. 1, an iontophoresis device includes a generator and controller system 10, which is connected via connecting components 12 and 14 to electrode assemblies 16 and 18. In use, the electrode assemblies are connected to a body or body part 20. Optionally, the system may also include a support system 22 that may help the user (who may or may not be a patient) to perform daily activities and/or improve other functions, e.g., by improving the connection between the electrode assembly or assemblies and the body or body part. Optionally, one or multiple masks 24, 26 may be attached to the electrode assemblies, so that during use they are positioned in between the electrode assembly or a part of the electrode assembly and the body or body part to protect certain parts of the body, or to drive the current preferentially to certain parts of the body.

This iontophoresis device may be wearable on a user's body. Wearability may help make the device more convenient to use. An iontophoresis device may be mains-powered, and hence not fully wearable. Mobility of the user during use may still be possible by making the connecting components between the generator and controller system and the electrode assembly or assemblies long, for example longer than 1 m in length, or longer than 5 m in length, or longer than 10 m in length. A non-wearable iontophoresis device may also comprise of an electrode assembly, electrode assemblies or a support system incorporated into one or multiple accessories or other attributes that are not traditionally wearable, including a steering wheel, a computer mouse, or a touchpad. The electrical circuit may be completed when the user makes contact with the accessory or other attribute in which the electrode assembly or assemblies is incorporated.

Two or more components and/or subsystems of the iontophoresis device may be integrated into one another. To give just a few examples, the connecting components 12 and 14 can be integrated into the support system 22, the generator and controller system 10 can be integrated into the support system 22, the masks 24, 26 can be integrated into the electrode assemblies 16 and 18, the connecting components 12 and 14 can be integrated into the electrode assemblies 16 and 18, or the connecting components 12 and 14 can be integrated into the generator and controller system 10, or a combination of any of these options.

Figure 2:
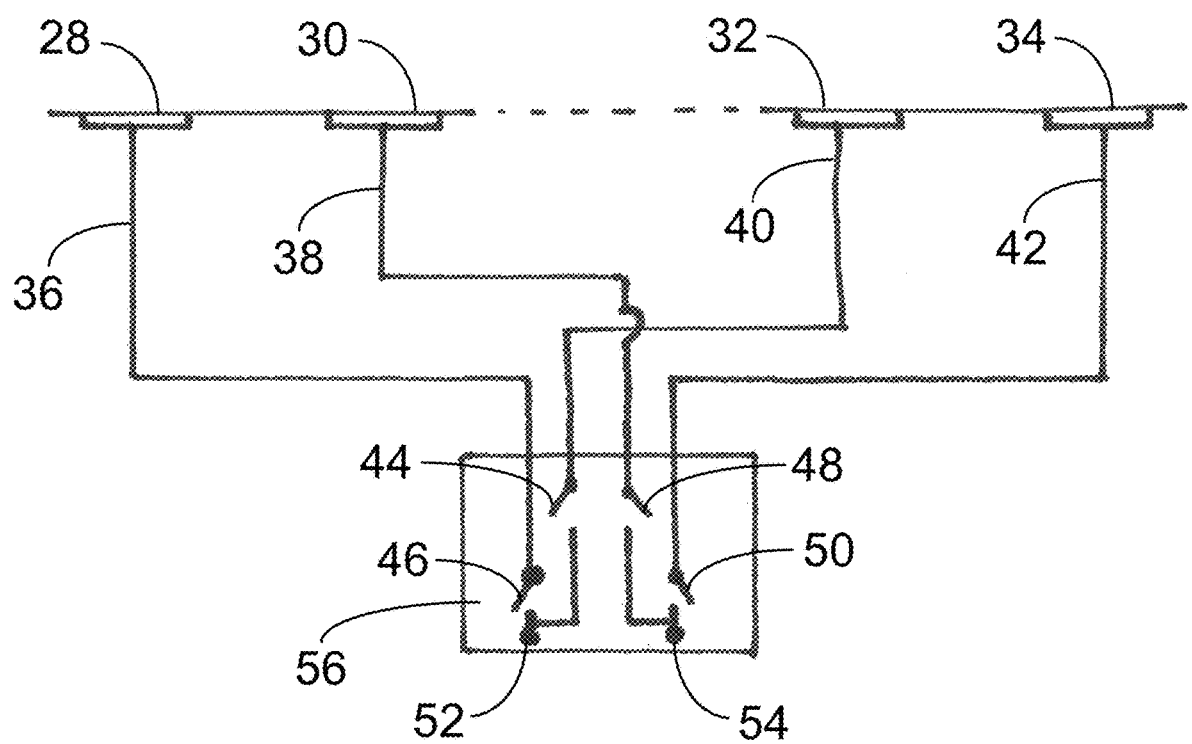
FIG. 2 is a schematic drawing of an iontophoresis device that contains multiple electrical circuits, according to an embodiment of the invention.

As shown in FIG. 2, the iontophoresis device may include multiple electrode assemblies 28, 30, 32, 34 that can independently be activated to create different circuits with connecting components 36, 38, 40, 42, allowing current to run in different trajectories through the body or body parts. This is illustrated in FIG. 2 for two electrical circuits with switches 44, 46, 48, 50 placed along bifurcated leads emerging from the electrical terminals 52, 54 of the power generator 56. It is also possible to have multiple generator and controller systems drive separate electrical circuits.

Electrode Assemblies

Electrode Assemblies: Purpose

The electrode assembly or assemblies form(s) the interface between the iontophoresis device and the body or body part(s) to which the electrical current is delivered. They fully or in part conduct the electrical current to the pre-selected current delivery area.

Electrode Assemblies: Form Factor

The electrode assemblies can be connected to any part of the body, including the hand, palm, back of the hand, wrist, foot, sole, top of the foot, ankle, armpit, arm, leg, groin, face, neck, back, or chest. The electrode assembly design can help ensure effective delivery of electrical current to a pre-selected current delivery area, as defined by the outline of the electrode assembly.

According to one embodiment, the electrode assembly may be one or multiple pads covering a body part containing the pre-selected current delivery area. In the case of a treatment, the pre-selected current delivery area may be the treatment area. It is also possible that only one or a few of the electrode assemblies are placed over a treatment area, and that the other electrode assemblies are placed elsewhere, for example a wrist, a forearm, an upper arm, a leg, etc. This position may be adjustable to increase convenience for the user. The electrode assembly dimensions can be customized to a specific individual's dimensions, or can be made in a range of standard sizes based on one or multiple key dimensions of the body part. For example, for the hand this could be the hand breadth, palm breadth, hand length, palm length, dorsum length, finger thickness, finger length, digit-to-crotch height, or hand circumference. For the foot this could be the foot breadth, foot length, instep length, or ball-to-foot circumference. For the face this could be chin-hairline distance or ear-to-ear distance.

Figure 3:
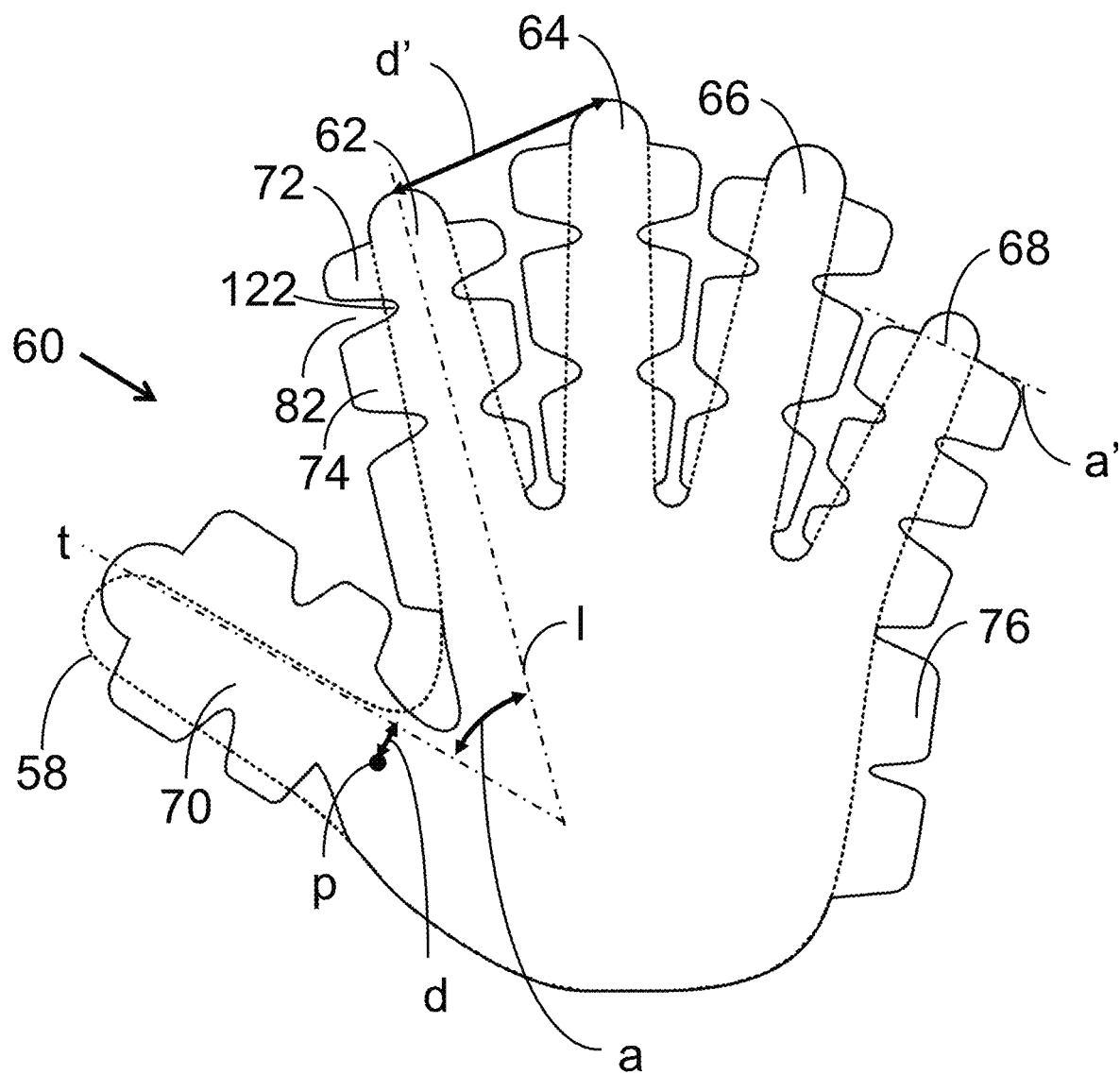
FIG. 3 illustrates the overlay of a pad representing a simple hand print (dashed line) and a hand-shaped pad adjusted to cover the parts of a hand that contain eccrine sweat glands (solid line), according to an embodiment of the invention.

According to one embodiment, an electrode assembly is partly or entirely constructed from one or more two-dimensional pads that (together) adequately cover (a portion of) the pre-selected current delivery area when folded or curved into a three-dimensional shape. This may improve manufacturability of the electrode assembly or assemblies, as the manufacturing of a three-dimensional structure would be more difficult. For example, as illustrated in FIG. 3 (dashed line 58), a manufacturable embodiment of a pad for the palm could be the simple projection of the palmar side of a hand onto a two-dimensional surface. As illustrated in FIGS. 4A-B, while this shape may provide coverage for the pulp of the fingers 78 and the central portion of the palm, it would not provide the same coverage for the palmar side of the proximal and distal phalanges of the thumb 80. Given human hand anatomy, in a projection of the palmar side of a hand onto a two-dimensional surface, only the outer side of the thumb would be projected. This is suboptimal and sometimes undesirable for the management of hidrosis or treatment of palmar hyperhidrosis, given the palmar side of the proximal and distal ("pulp") phalanges of the thumb 80 can sweat significantly.

According to one embodiment for a palm, as is illustrated in FIG. 3 (solid line 60), a two-dimensional pad could be constructed to adequately cover the palm of a hand and the palmar side of the thumb, when folded or curved into a three-dimensional shape. This two-dimensional pad 60 is hand-shaped, having four finger-shaped protrusions 62, 64, 66, 68, and a thumb-shaped protrusion 70. Compared to the simple projection of the palmar side of a hand onto a two-dimensional surface 58, the thumb-shaped protrusion 70 of the hand-shaped pad 60 may be translated perpendicular to its longitudinal axis 1 towards the adjacent finger-shaped protrusion 62, or in the direction of the adjacent finger-shaped protrusion 62, to ensure the palmar side of the proximal and distal ("pulp") phalanges of the thumb 80 will be adequately covered once placed on a hand. This may be achieved by separating the longitudinal axis t of the (distal section of the) thumb-shaped protrusion 70 by a distance d of 2 mm or more from the midpoint p of the thumb-shaped protrusion at the base of the thumb-shaped protrusion 70. The hand-shaped pad 60 may include one or more tabs 72, 74, 76 on pad edges. At their distal ends, adjacent finger-shaped protrusions (e.g., 62 and 64) are separated by a distance d' equal to the sum of the width and half the thickness of a finger or more, such that the material between the finger-shaped protrusions may be used for the potential addition of tabs (e.g., 72, 74) on the pad edges and other features, thereby improving manufacturability. The thinner and narrower of the fingers corresponding to the finger-shaped protrusions is chosen as the reference for the calculation. For example, if a woman has an index finger of 1 cm in thickness and 1.5 cm in width and a middle finger of 1.1 cm in thickness and 1.6 cm in width, the minimal distance between the distal edges of the corresponding finger-shaped protrusions would be 2.0 cm (i.e., 1.0/2 cm+1.5 cm). Assuming that a finger thickness is about half its width near the nailbed, this formula may be approximated further. With this assumption, distal ends of adjacent finger-shaped protrusions of the four finger-shaped protrusions should be separated by a distance equal to 1.25 times a width of the narrower finger-shaped protrusion of the adjacent finger-shaped protrusions that excludes tabs on pad edges or more. The angle a between the longitudinal axis t of the thumb-shaped protrusion and the longitudinal axis 1 of the adjacent finger-shaped protrusion is 20° or more, such that the thumb-shaped protrusion 70 will cover the palmar side of the thumb 80 once folded or curved onto the hand, and such that the material between the thumb-shaped protrusion 70 and the adjacent finger-shaped protrusion 62 can be used for the potential addition of tabs 72, 74 on the pad edges and other features, such as connecting protrusions (e.g., 124) thereby improving manufacturability. The embodiment of FIG. 3 also features tabs along the side of the hand (e.g., 76).

If the pre-selected current delivery area is the sole of a foot, the two-dimensional pad(s) could also adequately cover (a portion of) the arch and the toes, when folded or curved into a three-dimensional shape. As is illustrated in FIG. 5A, according to one embodiment suitable for the sole of a foot 84, the tabs 86, 88, 90, 92, 94, 96 are placed around the outer perimeter of the sole print 98 on the pad edge to cover the sides of the foot. The outline of the embodiment illustrated in FIG. 5A follows the shape of the toe imprints. As illustrated in FIG. 5B according to another embodiment, this does not have to be the case. For this embodiment, the pad 102 does not have gaps between the toes.

Returning to FIGS. 3 and 5, to ensure good coverage of the pre-selected current delivery area, tabs 72, 74, 76, 86, 88, 90, 92, 94, 96 may be added to edges of an otherwise simple shape (e.g., hand print for the palm, foot print for the sole, circular or elliptic or other convex or concave shape for the armpit or face). For example, the electrode assembly or assemblies may be configured to cover some or all body parts that contain eccrine, apocrine, apoeccrine or other (sweat) glands. For the hand, these tabs 72, 74 may then be used to cover the sides and/or backs of the fingers, the sides of the hands 76, and/or the webs of the fingers. For the feet, these tabs 86, 88, 90, 92, 94, 96 may be used to cover the sides of the foot. These may also be used to cover the webs of the toes. Areas that are more sensitive, for example the nail beds, nose, eyes or sides of ankles, may purposefully not be covered. If two tabs are adjacent to each other (e.g., 72, 74 and 86, 88), they may be separated by a notch (e.g., 82). Such a notch (e.g., 82, 100) may help allow points of the electrode assembly to move relative to each other if the notch is located at or up to about 1.0 cm away from the location of an area of substantial body part movement, e.g. a joint or a skin crease.

Different tabs on the electrode assembly or assemblies of an iontophoresis device can have the same or differing shape and dimensions depending on the needs. The tabs uniformly within a given embodiment or individually each may be rectangular, trapezoidal, parallelogram-shaped, triangular, may have rounded and/or squared edges, may be arc-shaped, or may have a more complex shape to optimize for a variety of functions, including application or removal of the tabs, application or removal of other subsystems of the iontophoresis device (e.g., the support system or the generator and controller system), and connection to the body or body part. For example, the most distal lateral edge of each tab 72, 74, 76 in FIG. 3 is angled so that it will be easier to slide a glove onto the hand over the tabs, while the most proximal lateral edge of each tab 72, 74, 76 is angled so that it will be easier to slide the glove off the hand. As shown in FIG. 3 according to an embodiment for tabs on a finger-shaped protrusion, the angle a' between the lateral tab edge and the perpendicular of the longitudinal axis of the finger-shaped protrusion may be 5° or more, pointing away from the distal end of pad in the case of the distal tab edge, and pointing towards the distal end of the pad in the case of the proximal tab edge. Even if the tab is not rectangular, this overall orientation may be maintained. Similar angles may be defined for tabs on other pad edges to ensure it will be easier to slide the glove onto the hand. Similar features may be defined on electrode assemblies on other body parts, e.g. for the sole of a foot (making it easier to slide e.g., a sock or shoe over the electrode assembly) or for an armpit (making it easier to slide clothing over the electrode assembly).

For the embodiment of FIG. 3 for the hand, the pad(s) has finger-shaped protrusions 62, 64, 66, 68 that have a width substantially equal to a finger width; the tabs 72, 74 are separated by inwardly converging notches 82 at or up to about 1 cm away from the locations of the knuckles; and tabs 72, 74, 76 have a width substantially equal to triple the thickness of the covering body part or smaller. As illustrated in FIG. 6A for a finger 110, according to one embodiment, the tab of the electrode assembly 112 reaches to just below the middle line 114 of the finger, or higher, when folded or curved around the finger 110. As illustrated in FIG. 6B for the side of a palm 116, according to one embodiment, the tab of the electrode assembly 118 reaches the middle line 120 of the cross-section of the hand at that location, or higher. As is illustrated in FIG. 5A, according to one embodiment suitable for the sole of a foot 84, the tabs 86, 88, 90, 92, 94, 96 are placed around the outer perimeter of the sole print on the pad edge. The tabs are separated by inwardly converging notches (e.g., 100). These notches (e.g., 100) may be collocated with positions on the pad edge (excluding tabs) 98 where the first, second or higher order derivative of the pad edge changes sign, or may be positioned to obtain tabs of a desired length (for example shorter than 2 cm, shorter than 5 cm, or shorter than 8 cm), or a combination of both. For a foot, tabs on the side of the foot could have a width that allows the tab to fold or curve over the entire foot like a slide slipper, or could be as narrow as about 5 mm or less. Similar features may also be included in other embodiments for other body parts; e.g. for a face, or for an armpit.

The pad, garment, film, dressing or other electrode assembly embodiments may contain relief cuts to allow for a more comfortable user experience. To form the relief cuts material may be removed in locations where material may buckle during bending, or the material may not be added in these locations in the first place. For example, in the case of a finger as illustrated in FIG. 3, a relief cut 122 may be placed adjacent to finger joints (adjacent to locations of notches 82 between tabs 72, 74) to allow for more natural finger movement. Other possible locations for relief cuts on a hand-shaped pad are for example adjacent to the webs of the fingers, and adjacent to the knuckles.

An electrode assembly may contain additional features that can help connect the electrode assembly with the connecting components, or with the generator and controller system. As illustrated in FIG. 7, according to one embodiment for use on a hand, connecting protrusions 124 and 126 may be added as strips of material to the pads 128 and 130, and a length reaching to the connection point with the connecting devices components, or with the generator and controller system. These additional features may also be included in other embodiments for other body parts; e.g. for the sole of a foot, for a face, or for an armpit.

According to one embodiment, the electrode assembly may be customized by cutting or tearing off part(s) to shape. Cutting or tearing may be aided by predefined tear lines, for example implemented by small cuts along a predefined line or pre-stressing the material—where adjacent small cuts may be separated by about 2 cm or less. Different layers of the electrode assembly (illustrated in FIG. 13) may have tear lines at slightly different locations to prevent some layers from touching the body, body part, skin, membrane or other tissue. For example, the tear line on the conductive layer 224 may be further away from the original edge than the tear line on the insulation layer, thereby preventing skin/membrane/tissue burns.

According to one embodiment, the electrode assembly may be a garment or contained in a garment, such as a glove, a sleeve, a sock, a shirt, a face mask, a hat, a cuff, an armband, a leg band, a shoe, a shoe insert, a vest, an underarm strap, or a belt, or a section of a garment. The garment can be constructed out of a combination of insulating and conductive materials, with conductive materials covering at least the pre-selected current delivery areas.

According to one embodiment, the electrode assembly may be built into devices, tools, systems, that are used daily, weekly, monthly, frequently or infrequently by users, for example into a steering wheel, winter gloves, a mug, a computer mouse, a touchpad, or a tooth brush.

According to one embodiment, illustrated in FIG. 8 for a hand, the electrode assembly may be or may contain a thin flexible transparent conductive film 142 with one or multiple electrically conductive wires or tracings 144, 146, 148 to evenly distribute electrical current across the pre-selected current delivery area. For the hand 150, this film 142 may be applied to the pre-selected current delivery area. This configuration of a conductive film with conductive wires or tracing as illustrated in FIG. 8 may be used in other embodiments, e.g. for the treatment of the sole of a foot as shown in FIG. 5.

According to one embodiment, the electrode assembly may be or may contain a conductive polymer or other material that can be distributed over the pre-selected current delivery area. Once this conductive polymer or other material has dried in place, it creates a continuous film covering a region of body part through which electrical current can be delivered.

Electrode Assemblies: Configurations

In an embodiment shown in FIG. 9, designed for use with a hand 162, multiple electrode assemblies 152, 154, 156, 158 can be used in series or in parallel, or a combination of both, to optimize for various outcomes, including body (part) movement, sensation, desired electrical current delivery pattern (e.g., with the intent of optimizing treatment level on the various body parts) or manufacturability. Such multiple electrode assemblies may be used with embodiments designed for use with other body parts, including, e.g. the sole of the foot, the face, the armpits.

The shapes and dimensions of the electrode assemblies 152, 154, 156, 158 can be chosen based on the position of one or more major or minor palmar creases (e.g. 160), areas of natural skin folding, or areas of large skin displacements during hand movement, with the potential goal of maintaining natural hand movement. As illustrated in FIG. 7, according to one embodiment, this may be achieved by having one electrode assembly 128 that is shaped in the form of a base having four finger-shaped protrusions 132, 134, 136, 138, and another electrode assembly 130 that is shaped in the form of a palm having a thumb-shaped protrusion 140. By separating the electrode assemblies in this way, one or multiple additional tabs may be added on either electrode assembly to cover the side of index finger facing the thumb, or connecting protrusions 124, 126 may be added on either or both electrode assemblies. According to another embodiment, as illustrated in FIG. 10, one electrode assembly 170 may be shaped in the form of a section of a palm having one thumb-shaped protrusion 174 and two finger-shaped protrusions 176, 178, and another electrode assembly 172 may be shaped in the form of the complimentary section of the palm having two finger-shaped protrusions 180, 182, with a separation line 184 in between. Similarly, for the foot, the electrode assemblies may be combined so that together they are sole-shaped. Other electrode assembly configurations are possible. According to another embodiment, one electrode assembly is shaped in the form of a base with four finger-shaped protrusions and a thumb-shaped protrusion, and a second electrode assembly is shaped in the form of a palm.

Electrode assemblies may be mechanically separate, connected through non-conductive materials or connected through conductive materials, for example on or adjacent to skin creases. If electrode assemblies are connected through conductive materials, for example through wiring or tracing, they together form one cathode or anode. In this case, the separation between adjacent electrode assemblies may be about 0 mm or larger. If a cathode is adjacent to an anode, the separation between adjacent electrode assemblies may be about 1 mm or larger.

Tapper (U.S. Pat. No. 4,164,226) mentions that a configuration of the anode and cathode upon a hand useful for inhibiting perspiration of the hand consists of the anode positioned upon the palm of the hand, and the cathode upon the fingers of the same hand. One would therefore expect that a placement of the anode on the 4 fingers (which often sweat more profusely than the rest of the hand), and a placement of the cathode on the palm and thumb would not result in an effective treatment. We have found, however, in an experiment, that the latter configuration does result in an effective treatment. We treated patients with palmar hyperhidrosis with a device set-up as illustrated in FIG. 11, with the anode 190 on the 4 fingers, the cathode 192 on the palm and thumb, and both electrode assemblies connected with a mains-powered generator 194 through wiring 196, 188 and the hand 198. One patient in this experiment received 14 days of treatment of their right hand 212 for 30 minutes daily at a current level of 9-12 mA, while their left hand 200 remained untreated. The data are visualized by an iodine imprint test for this patient in FIGS. 12A-B. The iodine imprint test consists of applying iodine to both palms, drying the hands, and then placing the hands on starch-containing paper for a period of 2 minutes. Wherever the patient sweats during the 2-minutes period, the paper will show a dark imprint. The paper will not or only minimally be stained where the patient does not sweat during the 2-minutes timeframe. For the patient described here, FIGS. 12A-B demonstrate that the patient's untreated hand 200 was still sweating on the entire imprint, while the treated hand 212 was mostly dry. Most importantly, the patient noted more confidence in daily life thanks to this improvement. This approach could also be used for the management of hidrosis. Other ways to optimize the location of the anode and the cathode besides management or treatment effect, could be safe current density (e.g., placing the cathode on thicker or sturdier skin) and sensation.

The anodal and cathodal sides could be changed around during different portions of the electrical current delivery session, either within one session or sitting, or after a number of sessions in the same configuration. It is also possible to exclude one or multiple electrode assemblies from the circuit during one or multiple sessions, for example to create a greater distance between active electrode assemblies or to allow a portion of the pre-selected current delivery area to get some "rest" (i.e. no energy delivery to this area for a period in time, e.g. a fraction of a second, minute (s), hour(s) or day(s)).

The electrode assemblies may be made available in one or more different sizes, and electrode assemblies of different sizes may be combined to achieve customizable fitting. For example, in the case of the embodiment illustrated in FIG. 7, the pad 128 with the finger-shaped protrusions may be available in up to 10 sizes, and the pad 130 with the thumb-shaped protrusion may be available in up to 10 sizes, resulting in a total of 100 possible sizes for the entire hand-shape. Finger-shaped protrusions may be rectangular, trapezoidal, parallelogram-shaped, triangular, may have rounded and/or squared edges, may be arc-shaped, or may have a more complex shape to optimize for a variety of functions. Finger-shaped protrusions of the same pad may have the same of or different lengths and widths. The length of a finger- or thumb-shaped protrusion can be about 1 cm or about 16 cm or any length in between. The width of a finger- or thumb-shaped protrusion (excluding tabs) can be about 0.5 cm or about 4 cm or any width in between. The manufacturer, healthcare professional, caregiver, user or other individual can combine the sizes that will be right for the user. For example, one may combine a pad with finger-shaped protrusions in which the longest finger-shaped protrusion is 9 cm with a pad in the form of a palm with thumb-shaped protrusion with a palm breadth of 8.8 cm, while one may also combine a pad with finger-shaped protrusions in which the longest finger-shaped protrusion is 8.5 cm in length with a pad in the form of a palm with thumb-shaped protrusion with a palm breadth of 9.5 cm.

The area of the anodal area may be equal to 33% to 300% an area of the cathodal area. For example, the relative surface area of the cathodal versus the anodal electrode assemblies within one (electrical) circuit may be 1:1, 2:1, 1:2, 1:3 or 3:1. A larger relative cathodal area may be used to optimize for safety, while a larger relative anodal area may be used to optimize for efficacy.

Electrode Assemblies: Materials

As illustrated in FIG. 13, an electrode assembly may include a stabilizing liner 220, an insulation layer 222, a conductive layer 224, a fuse layer 226, a carrier 228, an adhesive 230, a bottom liner 232, and an edge protection 234 or a subset of all these layers. The order of these layers can be different from the one listed here depending on the desired configuration. For example, the fuse layer and the conductive layer may be swapped compared to what is shown in FIG. 13. The layers can all have the same shape and size, or have different shapes and sizes. The layers can also be made out of multiple parts, and the shape, size and location of the parts for one layer do not need to be the same as the shape, size and location of the parts for any other layer.

The stabilizing liner 220 may be used to hold together the electrode assembly when not in use, and may either stay on or be peeled off once applied to the body or body part. The stabilizing liner 220 may be made out of plastic or any other material with a minimal amount of structure to it.

An insulation layer 222 may line the conductive layer 224 to avoid the user directly contacting the conductive layer once the stabilizing liner has been removed. This insulation layer 222 may be made out of any material that is insulating to the electrical current that the electrode assembly can deliver, including plastic, rubber, glass, or any composite of the above. Because flexibility is also desirable, thin plastics films such as polyethylene film, polyester film, polypropylene film, nylon would be most preferential.

The conductive layer 224 may contain carbon, tin, copper, lead, aluminum, platinum, silver or any other conductive material. Instead of producing this layer as a conductive sheet, alternative designs may be employed, for example to reduce material cost, including wiring or (flexible) traces.

A fuse layer 226 may be included to serve as a protection against low or high energy levels, currents, voltages or a combination of parameters. The fuse layer 226 may contain materials or assemblies whose resistance, impedance and/or other characteristic is dependent on one or multiple variables, for example heat, current, or voltage. The fuse layer 226 may be a continuous layer, or rather include discrete zones of material that will temporarily or permanently develop a high or infinite resistance to (electrical) current, and these zones may be isolated by empty space or by materials that are fully non-conductive or conductive.

A carrier 228 may be applied to the body part, or to the electrode, pad or garment, to aid in electrical current delivery. The carrier 228 may be a liquid (e.g., a solution such as salted water, a suspension, or an emulsion), a semi-solid (e.g., a gel, a lotion, a cream, or a hydrogel). Sweat may also be a component of the carrier 228 to provide ionic communication between the electrode assembly or assemblies and the body or body part. In case of a garment, the garment may be sealed at the ends to avoid the carrier 228 from leaking out, or the carrier may be immobilized within the garment using an absorbent material (e.g., gauze, sponge). The carrier may contain other additives such as a pH buffer (to help prevent tissue burns). The carrier may also contain drugs or active agents.

An adhesive 230 may be used to ensure connection between the electrode assembly and the body or body part. The adhesive 230 can be mixed in with the electrolyte composition, or carrier 228, or can be added on separately. Numerous different types of adhesives 230 can be used, including acrylic adhesive, cyanoacrylates.

A bottom liner 232 may be used to ensure structural rigidity during manufacturing, and may be used to protect the adhesive layer and/or carrier during packaging. The bottom liner 232 is removed prior to application to the body or body part.

The edges of the electrode assembly may be finished with an additional insulating material 234 to prevent skin, membrane or other tissue burns. Burns may also be prevented by applying a non-conductive gel (e.g., petroleum jelly) or other material to the cut edge. As illustrated in FIG. 13, this edge protection 234 may surround the insulation layer 222, the conductive layer 224, the fuse layer 226, the carrier 228 and potentially the adhesive 230. Alternatively, this edge protection 234 may sit in between these layers of adjacent electrode assemblies, without extending above the top and bottom layers of this list. Alternatively or additionally, this edge protection 234 may be continuous with the insulation layer 222.

The electrode assembly may also include elements that allow the user to still manipulate capacitive touchscreens and other electronic equipment, for example through the addition of conductive thread or other materials that mimic the capacitive properties of human skin.

Additional material may be added on one or more sections of the edge of the electrode assembly to allow easy application and removal of the electrode assembly to the body (part). One embodiment of this may take the form of one or multiple non-conductive (e.g. plastic) pull tabs on the edge of the electrode assembly.

According to one embodiment, one or multiple zones may be indicated on the electrode assembly with a marker, coloring, a different material or material thickness, writing or other means. These zones could indicate where additional material may be applied by the user, for example where drugs or active agents may be applied for active agent/drug delivery (e.g., antiperspirants, in particular aluminum-containing ones such as aluminum chlorohydrate or aluminum-zirconium), or where petroleum jelly may be applied.

The tabs (e.g., 72, 74, 76) and connecting protrusions (e.g., 124, 126) can be made out of the same or different material as the rest of the electrode assembly, may have conductive areas or non-conductive areas or both, and may be adhered to the body or body part using an adhesive or mechanical means of ensuring conformity with the body or body part, for example with a material or geometry that can have a preferred state such as nitinol or a layered, flexible stainless steel bi-stable spring bands sealed within a fabric, silicone, or plastic cover. Alternatively or additionally, securing of the tabs may be ensured by the support system. For the embodiment illustrated in FIG. 7 for a hand, the parts of the connecting protrusions contacting the back of the hand may be made out of a non-conductive material, or have a mask with a non-conductive material, while the other parts of the connecting protrusions (e.g., sides of the hand) are conductive to ensure delivery of electrical current to these parts. In the case of management of hidrosis or treatment of hyperhidrosis this embodiment may be used to treat the parts of the hand that sweat most.

If two or more electrode assemblies are present in the iontophoresis device, as is the case in FIG. 9, the electrode assemblies 152, 154, 156, 158 may be mechanically separate, connected through non-conductive materials or connected through conductive materials. If connected through non-conductive materials, these materials could be materials including plastic, rubber, glass, or any composite of the above. Also thin plastics films such as polyethylene film, polyester film, polypropylene film, nylon and other flexible materials would be possible. If connected through conductive materials, these materials could be materials including metals, such as silver, gold, copper, nickel, ferrous alloys or alloys of any of the previous, or conductive polymers e.g., PEDOT or polyacetylene. These connecting segments could be following the same layered structure as the adjacent electrode assemblies, or could have a different set of layers. According to one embodiment, electrode assemblies are connected through non-conductive materials by using a continuous insulation layer for these electrode assemblies, while some or all other layers of the electrode assemblies are separated. In this case, some other layers may also be connected, for example the bottom liner and edge protection. Additional insulating material, e.g. in the form of a strip, may be placed on the carrier/adhesive side in the locations where adjacent electrode assemblies meet to ensure there is no electrical connectivity with the body in these locations.

If two or more electrode assemblies are present in the iontophoresis device, the materials used for these electrode assemblies or particular layers of these electrode assemblies can be the same or different. For example, by using a difference in carrier material 140 or thickness, conductivity can be different for the various electrode assemblies. This may also help optimize various outcomes, including body (part) movement, sensation or desired electrical current delivery pattern (e.g., with the eye on optimizing treatment level on the body part) or manufacturability. Also, for example, the fuse layers 138 of different electrode assemblies may be tuned differently so that different levels of electrical current are delivered to different body parts.

Electrode Assemblies: Manufacturing Details

An electrode assembly may be manufactured by layering the various layers onto one another in a sheet-like configuration. An electrode assembly may also be manufactured by layering most layers one after the other, and then adding in missing layers later on. An electrode assembly may be cut to shape manually, by using die-cutting tools, or other manufacturing techniques.

According to one embodiment, the electrode assembly is customized based on a model or a customized model of the pre-selected current delivery area to ensure a good connection between the electrode assembly and the body or body part. This customized geometry could be produced by any means of low volume electrode manufacturing, for example steel rule die cutting, or by rapid manufacturing techniques such as 3D printing.

Ensuring a Good Connection Between an Electrode Assembly and Body or Body Part

The connection between an electrode assembly and body, skin, membrane or other tissue, can be formed or improved in a number of ways. This connection is of critical importance, since it may for example affect sensation (e.g., tingling, feeling of pins and needles, muscle tightening) during and after electrical current delivery, as well as susceptibility to other side effects such as erythema and mild or severe burns. This connection may also be of critical importance for an easy-to-wear system, since the system should stay connected to the body part throughout (the majority of) the use session.

As mentioned elsewhere in this disclosure, the electrode assembly may contain an adhesive 230 to ensure connection between the electrode assembly and the body. An adhesive connection may be necessary on concave parts of the body, for example on the center of the palm for an embodiment on a hand, since other techniques to maintain a good connection may be less successful here.

According to one embodiment, the electrode assembly is secured to the body by an adhesive outer edge, that is at least as or more adhesive than the rest of the electrode assembly-body connection, to ensure the edges do not get disconnected from the body part. This may for example be achieved with an additional layer over the electrode assembly so that the outer perimeter of this new layer provides the secure electrode assembly-body connection. As another example, this may be achieved by adding adhesive sections over part of or over the full perimeter of the electrode assembly.

As illustrated in FIG. 3 and FIG. 5 for the hands and feet respectively, the connection between the electrode assembly and body or body part is improved by tabs (e.g., 72, 74, 76, 86, 88, 90, 92, 94, 96) placed along the edges of the pad.

As illustrated in FIG. 14, according to one embodiment, the connection between the electrode assembly and body is improved by creating a low pressure region or vacuum. One or more flexible electrode assembly sheets 236 are placed on or around the body part 238 and subsequently air 240 is sucked out between the sheet(s) and the body part. A non-permeable cloth, membrane, or other flexible material 242 may be used to ensure a closed compartment is formed around (parts of) the electrode assembly sheet(s) and body part, out of which the air can be sucked. Suction could be achieved through a pump, including manual or automatic pump, or an electrical pump.

According to one embodiment, the connection between the electrode assembly and body or body part is improved by applying pressure, either passively (e.g., through a tight-fitting garment around the electrode assembly) or actively (e.g., by applying hand pressure). This may be integrated with the support system. For example, for a glove support system, a compression glove or other compressive glove may be used.

According to one embodiment, the connection between the electrode assembly and body or body part is improved by using a stretchable and/or flexible electrode assembly, potentially in combination with a less stretchable and/or flexible element that is anchored to one part of the body. For example, rigid or non-rigid finger caps can serve as anchors for a thin flexible conductive film that is stretched out over the palm between the finger caps and a wrist-worn generator or a generator worn on the back of the hand.

According to one embodiment, the electrode assembly is applied to the body or body part like a bandage to ensure a good connection between the electrode assembly and the body part.

According to one embodiment, the electrode assembly may contain microneedles. This may allow the electrode assembly to bypass the relatively high electrical resistance of the outer most layer(s) of the body part, for example the stratum corneum or the dermis in case of the skin, thereby reducing the overall size of the electrode assembly required to achieve good electrical conductivity with the body or body part. This may also be used to increase contact surface area, instead of to bypass these outer most layer(s) of the body part, once again reducing the overall size of the electrode assembly required to achieve good electrical conductivity with the body or body part. Furthermore, this may reduce the amount of resistive heating generated, allowing for larger electrical current delivery doses without damage to the skin. The microneedles may be cylindrical, with circular cross-section, rectangular cross-section or any other shape of cross-section, and may be attached to a pad that have a conductive film or wiring to conduct the electrical current from the generator and controller system to the microneedles. The microneedles may be fully electrically conductive, or may have insulating portions or coatings. For example, to bypass the outer most layer(s) of the body part, the part of the microneedles closest to the pad to which they are connected may be covered by an insulating coating, as may be any parts of the pad that would otherwise be in contact with the body part. A commercially available microneedle patch may be used, or a microneedle patch with other dimensions or material characteristics may be used for this purpose.

Generator and Controller System

Generator and Controller System: Purpose and Use

The generator and controller system 10 ensures that the desired amount of electrical current and voltage is delivered to the body or body part. Even though iontophoresis devices often deliver direct current only, the electrical current may be alternating current, direct current, or a combination of both, for example through pulse width modulation or an alternating current with a direct current offset. The system may be current- or voltage-controlled, or neither or both. The system may have lower and/or upper limits built in for voltage and/or current, and/or related variables.

In the case of direct current, the current may start at about 0 mA or at any different current level, and be gradually increased and decreased as desired. This may occur in a stepwise fashion, as illustrated for an example in FIG. 15, or continuously, as illustrated for an example in FIG. 16, or a combination of both. The maximum current or current density may depend on what is still comfortable for a user. For example, a maximum current may be 5 mA for one user, while it may be 35 mA for another user. In the case this maximum current is selectable by the user the generator is able to respond to the user's inputs and modulate the delivered dose of current. In the case of alternating current, pulse width modulation or alternating current with a direct current offset, the same applies, but instead of using the direct current level, one should work with the root mean square or DC equivalent.

In the case there is an alternating current component, the frequency may be optimized to ensure minimal user discomfort. This optimal frequency can be user-specific, for example for one user the optimal frequency may be 5 kHz, while for another user the optimal frequency may be 10 kHz. The optimal frequency may be set by the user, or detected automatically, potentially with feedback from the user on sensation levels.

The system may be able to periodically reverse the polarity of electrode assemblies. As illustrated in FIG. 17, the current profile may also be an alternating current with a direct current off-set. This may be obtained through pulse width modulation.

The generator and controller system may be able to turn itself off at the end of the delivery time. The system may also include load monitoring to ensure the device is properly attached to electrode assemblies. The system may automatically switch off if no load is detected.

Generator and Controller System: Form Factor

In case the iontophoresis device is fully wearable, the generator and controller system 10 may be attached to any part of the body, including the hand, palm, back of the hand, wrist, foot, sole, top of the foot, ankle, armpit, arm, leg, groin, face, neck, back, or chest.

The generator and controller system 10 may be attached to the body separate from the electrode assemblies 16, 18 or connecting components 12, 14 or support system 22 or it may be connected to or integrated with one or multiple of said devices or systems. If the generator and controller system 10 is worn separate from the electrode assemblies 16, 18 or connecting components 12, 14 or support system 22 it may be attached to the body with adhesive or fastened around an appendage, for example a wrist. As illustrated in FIGS. 18A-B, according to one embodiment, the generator and controller system 250, is connected to two electrode assemblies 252 (on the hand) and 254 (on the forearm) through connecting components 256 and 258. The generator and controller system 250 is attached to the wrist. As illustrated in FIG. 19, according to one embodiment, the generator and controller system 260 is connected to two electrode assemblies that are incorporated in a pad 262 (on the hand). The connection is obtained through connecting components 264 and 266. The generator and controller system 260 is attached to the wrist.

The generator and controller system may take any shape that is most suitable for the particular application and location on the body. For example, in the case of a hand 268, as illustrated in FIG. 20, the generator and controller system 270 may be designed to fit well on the backside of the hand 268, which may include any location from the knuckles down to and including the wrist or beyond. This system 270 could be rectangular, circular, oval, with sharp or round edges, or any other shape.

Generator and Controller System: Components and Materials

The generator and controller system 10 is comprised of a generator and a current- or voltage-controlling circuit. The generator and controller system 10 is connected with the electrode assembly or assemblies 16, 18 through connecting components 12, 14.

The generator and controller system 10 may be battery-powered, AC mains-powered, capacitor-powered, or powered by an electricity-generating chemical half-cell reaction such as a galvanic cell using elements including silver, titanium or zinc. According to one embodiment, the generator uses a lithium-ion or lithium polymer battery, which provides the highest stored energy density that is commercially available at present.

The electricity-controlling circuit may be a simple current-limiting device that prevents voltage or current from increasing above pre-set thresholds even if load resistance is reduced. The electricity-controlling circuit may also be a feedback-controlled system to maintain a steady current output despite positive or negative changes in resistance of the load. Appropriately controlling current delivery to the body may additionally require knowledge of the surface area this electricity is being applied over. This allows a safe and efficacious current density to be maintained across any portion of the treatment area. The contact area between the body part and the electrode assembly is known from the sizing of the electrode assembly. By using electrodes of a fixed and predetermined surface area, the current density may be calculated and controlled, allowing standardization across users with different hand sizes. Since the contact area between the body part and the electrode assembly may be different for different users, current density may be different even if current is kept the same between different users. The surface area may be preprogrammed in the generator and controller system. The surface area may also be entered or overridden by the healthcare professional, manufacturer, user, caregiver or other individual, e.g., prior to shipping or prior to the use session. The surface area known if the generator and controller system is able to recognize the electrode assembly being used for the use session, for example through executable instructions stored in memory.

Both limiting and active control approaches to modulating current or current density can be done with either analog or digital circuit design. In the case of a digital control approach, the system requires current sensing on the outputs of the device, which can be feedback to a microcontroller running a control loop (such as a PID controller) to drive a voltage source output higher or lower to maintain current a set current. The controller circuit may include a digital processor with executable instructions stored in memory. The instructions may include instructions to automatically limit delivered current, voltage, and/or current density to below selectable, predetermined thresholds.

The generator and controller system 10 may also include an interface to allow the user to make adjustment to the system's output voltage, current or to the control characteristics of the voltage or current output. This interface could be a power switch to turn the device on or off, or an internal accelerometer that detects movements of the user's body part to provide gesture-based control of various settings. For example, for the hand, rapid hand motion may be detected by an accelerator and cause the device to switch off. The system may also provide information to the user via visual or auditory messages through devices such as an incorporated screen, lights, a speaker, or combinations thereof. As illustrated in FIG. 25, according to one embodiment, the system 314 has a small LCD or OLED touchscreen display 312 with 2 or more programmable buttons to allow a user to navigate a simple graphical user interface.

The generator and controller system 10 may also include a wireless transceiver (using 802.11x wi-fi, BLUETOOTH, BLUETOOTH Low Energy (BLE), near-field communication (NFC), optical or other wireless standards/protocols) to allow the system to interact with other generator devices or with other computing devices including a personal computer, a mobile phone, a wearable computing device (e.g. smartwatch), or tablet computer. This would allow data from use sessions to be recorded and transmitted for use (e.g., data review, data analysis) on other devices. The ability for the generator to communicate with devices such as a mobile phone would allow the mobile phone's display and interface to be used instead of placing a user interface directly on the generator as described above. The wireless transceiver may be integrated into the circuit board of the generator. Alternatively, the generator and controller system, or part of the generator or controller system, may be integrated into a personal computer, a mobile phone, a wearable computing device (e.g., smartwatch), tablet computer, or other generator and/or computing device.

The generator and controller system may also have a housing to protect the electronic components from damage. This housing may include a hard housing surrounding the circuit board and components. This housing may be made from materials including metal or plastic such as ABS, polycarbonate, or polyamides (e.g., nylon), or other (semi-)rigid materials. The housing may also be constructed of flexible, impact-absorbing materials such as various rubber- and silicone-based compounds, aramids, etc. The housing may exist as a standalone unit that interfaces with other components of the system, or may be incorporated into the other components of the system, for example, within the support system.

Generator and Controller System: Manufacturing Details

The generator and controller system may be manufactured according to techniques known in the art. This may involve printing a printed circuit board (PCB), that may have any shape in combination with a generator that could be positioned on top, below, next to, surrounding or integrated within the PCB. Typically, the generator and controller system will be contained in a housing that is sealed reversibly or irreversibly.

Connecting Components

Connecting Components: Purpose and Use

The connecting components connect the generator and controller system with the electrode assemblies.

Connecting Components: Form Factor and Components

The electrode assemblies 16, 18 and the generator and controller system 10 may be connected to each other directly, or indirectly through e.g., wiring or traces that connect a point or zone on the conductive layer 224 of the electrode assembly to the anode or cathode of the generator and controller system.

As illustrated in FIG. 7, according to one embodiment, the connecting components may take the form of connecting protrusions 124, 126 that may be integrated into the electrode assemblies. Connecting protrusions may be added as strips of material of a length reaching to the connection point with other connecting components, or with the generator and controller system. As illustrated in FIG. 20 for a hand 268, according to one embodiment, the connecting protrusions 272, 274 may be used to help secure the generator and controller system 276 on a hand 268.

As illustrated in FIGS. 21A-C according to one embodiment, the electrode assembly 276 and the generator and controller system may be connected to each other through conductive connectors or zones 278, 280 on either or both devices/systems, or on an additional garment or device that is in turn connected directly or indirectly (e.g., with wiring or traces) to either or both systems. These conductive connectors or zones 278, 280 of the same or different relative size may be aligned with the help of magnets, (electrical) snaps, lamination, solder, post connectors (e.g., 2 mm banana plug connectors), conductive fabric hook and loop fasteners, or any other alignment device or system or combinations thereof. If the conductive zones are different in size, alignment in various relative positions is possible. The conductive zone 280 on one side, for instance the generator and controller system side, is larger than the connector 278 on the other side, for instance the electrode assembly side, allowing for proper electrical connection in various relative positions. Two different relative positions that allow for proper electrical connection are shown in FIGS. 21B-C.

Another way to allow for various relative positions, is by placing multiple female or male connection parts on either the generator and controller system 10 or the connecting components 12, 14 or both. For example, in the case of connecting protrusions and snap buttons, multiple female snap button parts could be placed on one of the connecting protrusions, with one male snap button part on the generator and controller system. The snap button part on the generator and controller system may have two coaxial zones connecting to the anodal and the cathodal poles of the generator respectively. Once aligned with the snap button part of the generator and controller system, the female snap button parts on one of the connecting protrusions line up with the anodal coaxial zone, and the female snap button part on the other connecting protrusion lines up with the cathodal coaxial zone, or vice versa.

Connecting Components: Materials

Conductive elements of the connecting components could be made from any conductive material, including metal, such as copper, nickel, silver, gold or combinations thereof such as gold-plated or nickel-plated conductive contacts. The connecting components may also contain insulating materials, for example plastic or rubber, potentially in the form of a coating. For example, conductive contacts may be covered by an insulating shroud to prevent accidental contact with a body part.

Support Systems

Support Systems: Purpose and Use

The overall purpose of the support system 22 is to help enable the user to perform daily activities. This may involve, amongst others, holding some or all subsystems of the iontophoresis device together, forming or improving the connection between the electrode assembly or assemblies and the body or body part, improving the look and feel of the iontophoresis device, simplifying use for the user (including application and removal of the iontophoresis device), and enabling the user to execute daily activities. One or more of these purposes may also become the main purpose, for example the main purpose may be to improve the connection between the electrode assembly or assemblies and the body or body part, instead of enabling the user to perform daily activities.

Support Systems: Form Factor and Components

The support system 22 can take many forms, including wiring, a garment, such as a glove, a sleeve, a sock, a shirt, a face mask, a hat, a cuff, an armband, a leg band, a shoe, a shoe insert, a vest, an underarm strap, or belt, or a section of a garment. Interpretations of this nomenclature may be taken broadly. For example, a glove may be a normal glove, but also a glove with an opening on the backside of the hand, a glove without fingertips (such as or similar to a bicycling glove), a glove that consists of just a few straps of material, a golf glove, a driver's glove, an archery glove, a mitten, a gauntlet, a fingerless glove with mitten top, a fingerless glove with individual finger flaps/zippers, or any other variation of a glove. For example, a sock may be a normal sock, but also a sock with toes, an ankle-less sock, a heel-less sock, a slipper sock, a flip flop sock, a half-toe sock, a sock with open dorsal part, or any other variation of a sock. The garment may be manufactured without seams to help prevent non-uniform contact between the electrode assemblies and the body part, or seams may be placed on the outside of the garment as is sometimes the case for a compressive garment. According to one embodiment, as illustrated in FIG. 22, the support system 284 is a glove that is connected to the generator and controller system 286 through a snap button, while the generator and controller system 286 is connected to the electrode assemblies through wiring 288, 290. Other ways of connecting the support system to the generator and controller system include snap buttons, hook and loop fasteners, hooks, or a turning knob. As is illustrated in FIG. 23, the connecting components 292 connecting the generator and controller system 294 with the electrode assemblies may be integrated into the support system 296.

The support system may include elements that allow the user to still manipulate capacitive touchscreens and other electronic equipment, for example through the use of conductive thread or other materials that mimic the capacitive properties of human skin. This may for example be done on the fingertips according to an embodiment for the hand.

Features may be added to the support system to allow ready application and removal of the iontophoresis device, of the support system, or any other subsystem of the iontophoresis device. The support system may be equipped with one or multiple features such as zippers, hook and loop fasteners, or snap buttons. Additional sections of material may be added on one or more sections of the edge of the support system. According to one embodiment for the hand, this may take the form of one or multiple pull tabs adjacent to the wrist. According to another embodiment for the hand, this may take the form of a zipper placed on the lateral or dorsal side of the hand, extending from the wrist to the base of the finger.

The support system may cover or include part of the iontophoresis device, or the iontophoresis device in its entirety. For example, it is possible that one set of electrode assemblies is covered by the support system, but not the other electrode assemblies that are part of the system.

Support Systems: Materials

The support system may be made of any material that is non-conductive, or a combination of materials that is conductive and non-conductive. For example, the support system may be made of a woven or non-woven fabric that may be washable such as cotton, rayon, polyester, other polymer fibers. The material may be flexible to conform to the body part the support system is applied to. The support system may add light compression/pressure to the body part and/or electrode assembly and thereby improve the connection between body part and electrode assembly (e.g., compressive garment). The material may be capable of absorbing carrier.

Mask

Optionally a mask 24, 26 can be placed in between the electrode assembly or a part of the electrode assembly and the body or body part. This may be to protect certain parts of the body, or to drive the electrical current preferentially to certain parts of the body. The mask can comprise of petroleum jelly, silicon grease, rigid or moldable polymer, various rubbers, plastic film, or any non-conductive material.

Additional Methods for Minimizing Side Effects

Passive or active measurements may be performed to aid in the minimization of side effects, including tingling, feeling of pins and needles, muscle tightening, erythema or mild or severe burns. Potential variables to measure are temperature, pH, current level, voltage level, electrical resistance or impedance, amongst others. As illustrated in FIG. 24, according to one embodiment, one or multiple sensors 300, 302, 304 to measure one or multiple of said variables may be attached to or embedded in the electrode assembly 306. The sensor system 308 may be separate or integrated with the generator and controller system 310. For example, temperature under or adjacent to the electrode assembly may be tracked to identify risk of mild or severe tissue burning. If multiple electrode assemblies are being used, one or more, or a portion of one, may be switched off in case potentially damaging levels are being measured. Alternatively, the device may be switched off entirely in this case. The sensor output may be used to optimize dose settings through a feedback loop that is either mediated by the user or automatically handled by the generator and controller system. This open or closed feedback loop may rely on machine learning algorithms. Additionally, safety shut offs can be included to limit or stop electrical current delivery if dosing reaches unsafe levels.

Iontophoresis Device (Continued)

Iontophoresis Device: Purpose and Use

The user may deliver electrical current to his/her or someone else's body for any duration in time and can do this only once or multiple times. Particularly for the management of hidrosis or treatment of hyperhidrosis, the current can be applied on a daily basis, multiple times per day, on a weekly or monthly basis or at any other regular or irregular intervals. The current delivery may also be done overnight for the full duration of, longer or shorter than the time the user is in bed or asleep. The dose of current or current density delivered to the body can be monitored, logged and tracked over a single use session and/or over successive use sessions. Based on this information, recommendations of usage and dosing levels may be provided to the user. Methods for minimizing side effects may be used here, as described elsewhere in this disclosure.

The reduction in sweat response may happen during or immediately after the session. The reduction in sweat response may also be more pronounced some time (e.g., minutes, hours, days, weeks) after the use session.

The use sessions may be performed in a hospital, clinic, doctor's office, dermatologist's office or other healthcare setting, at home or a combination thereof. The management or treatment may be started in the healthcare setting and then move to the home setting after one or multiple use sessions. Alternatively, some or all use sessions may be performed in non-healthcare settings, including on the bus, while walking, while exercising, in the car, at the office, or in the kitchen.

The current and voltage settings may be kept constant or may be changed in between the sessions. The settings may be chosen freely or may be chosen based on information about the user's sweat response. As illustrated in FIG. 25, the user may set the settings through an analog or digital interface 312 on the generator and controller system 314 (which in this case is connected to the support system 316). The settings may also be set through other signals, for example motion. For example, according to one embodiment, hand gestures may be used to change the settings as captured from e.g., a wearable device housing, an accelerometer or a gyroscope. Also, sweat level testing may be performed in between use sessions, or the sweat levels may be assessed during use sessions. Sweat level testing may be obtained using one or a combination of techniques, including gravimetry, Minor's test, evaporimeter, other humidity sensors, Persprint paper testing, Hyperhidrosis Disease Severity Score questionnaire, Dermatology Quality of Life Index, visualization of individual or multiple sweat glands, sympathetic/galvanic skin response, electrical resistance measurement. These test results can be used to optimize dose settings through a feedback loop that is either mediated by the healthcare profession, user, manufacturer, caregiver or other individual or automatically handled by the generator and controller system. For example, current levels could be increased if the sweat levels are not decreasing after the first couple of use sessions and if the user does not indicate sensation is bothersome. The current levels could also be decreased once sweat levels have decreased to a possibly pre-determined level. This feedback loop would allow users to get adequate efficacy of the management or treatment while using the lowest dose and session duration. This open or closed feedback loop may rely on machine learning algorithms. The sweat levels may also be communicated to the user, for example—as illustrated in FIG. 26—through a user-interfacing device 318 to motivate the user to continue to use the devices and systems 320. This user-interfacing device 318 may be a computing device such as a mobile phone, a tablet, a wearable computing device (e.g., smartwatch), a laptop, a desktop personal computer, or any other device that has a user interface.

The total dose D (expressed in mA-min per cm$^2$), the iontophoresis device delivers, may be the same or different for different usage sessions. The total dose for a use session is defined as $$D_{anode} = \int_0^{\Delta T} \left(\frac{i(t)}{A_{anode}}\right) dt$$

where $D_{anode}$ is the total dose at the anode; $A_{anode}$ is the anodal surface area; $i(t)$ is the current level; $i(t)/A_{anode}$ is the current density, which should remain below a certain threshold, for example below about 1 mA/cm$^2$ for the majority of the usage time. Particularly for the cathode, the limit on current density may be set to a lower value, for example about 0.5 mA/cm$^2$ (Belanger 2010, Therapeutic Electrophysical Agents: Evidence Behind Practice. Philadelphia, Lippincott Williams and Wilkins); $\Delta T$ is the usage time, which can range between about 0 min and about 1440 min, or even larger if the session is run over multiple days.

A similar formula can be constructed for the total dose at the cathode $D_{cathode}$, where $$D_{anode} A_{anode} = D_{cathode} A_{cathode}$$

If $i(t)$ remains mostly constant (i) throughout the use time, the formula for $D_{anode}$ can be simplified to:

$$D_{anode} = \frac{i}{A_{anode}} \Delta T$$

If $i(t)$ is variable, the root mean square I may be taken.

According to one method, the total usage time $\Delta T$ and upper limit for current density are set by the healthcare professional, manufacturer or caregiver, the surface area $A_{anode}$ is known, and the current is set by the user. If the current density passes the allowed upper limit, the current is overridden by the iontophoresis device.

According to one method, the total dose D and upper limit for current density are set by the healthcare professional, manufacturer or caregiver, the surface area A is known, the current is set by the user, and the total usage time $\Delta T$ is calculated by the iontophoresis device according to the above formula. If the current density passes the allowed upper limit, the current is overridden by the iontophoresis device, and the total usage time $\Delta T$ is recalculated.

According to one method, the total dose D and upper limit for current density are set by the healthcare professional, manufacturer or caregiver, the surface area A is known, total usage time $\Delta T$ is set by the user, and the current is calculated by the iontophoresis device according to the above formula. If the current density passes the allowed upper limit, the current is overridden by the iontophoresis device and the total usage time $\Delta T$ is recalculated.

A kit may be assembled containing one or multiple iontophoresis devices, or any combination of the components or (sub)systems of the iontophoresis device described in this disclosure.

According to one embodiment, there is provided a kit which may be used for management of hidrosis or treatment of hyperhidrosis, the kit including: (a) one or multiple pads which include a set of electrode assemblies, each pad comprising a conductive layer and an adhesive hydrogel, and optionally tabs on pad edges; (b) a power source (wearable or not).

According to one embodiment, there is provided a kit which may be used for management of hidrosis or treatment of hyperhidrosis, the kit including: (a) one or multiple pads which include a set of electrode assemblies, each pad comprising a conductive layer and an adhesive hydrogel, and optionally tabs on pad edges; (b) a support system; (c) a power source (wearable or not).

According to one embodiment, there is provided a kit which may be used for management of hidrosis on the hands or treatment of palmar hyperhidrosis, the kit including: (a) two hand-shaped electrode assembly pads comprising tabs on pad edges, a conductive layer and an adhesive hydrogel; (b) a glove support system; (c) wiring to connect the two hand-shaped electrode assemblies; (d) a wearable power source.

According to one embodiment, there is provided a kit which may be used for management of hidrosis on the feet or treatment of plantar hyperhidrosis, the kit including: (a) two sole-shaped electrode assembly pads comprising tabs on pad edges, a conductive layer and an adhesive hydrogel; (b) a glove support system; (c) wiring to connect the two sole-shaped electrode assemblies; (d) a wearable power source.

According to one embodiment, there is provided a kit which may be used for management of hidrosis on the hands or treatment of palmar hyperhidrosis, the kit including: (a) two pads which each include a first electrode assembly in the form of a base having four finger-based protrusions and a second electrode assembly in the form of a palm having a single thumb-shaped protrusion. The two electrode assemblies of each pad may be connected to each other with a non-conductive material. One of the pads is for a left hand, the other one is for a right hand; (b) two glove support systems (one for a left hand, the other one for a right hand); (c) two wearable power sources. The kit could also be for just a left hand, or just a right hand, in which case only one pad is included, one glove support system, and one wearable power source.

According to one embodiment, there is provided a kit which may be used for management of hidrosis on the feet or treatment of plantar hyperhidrosis, the kit including: (a) two sole-shaped pads which include each two electrode assemblies. The two electrode assemblies of each pad may be connected to each other with a non-conductive material. One of the pads is for a left foot, the other one is for a right foot; (b) two sock support systems (one for a left foot, the other one for a right foot); (c) two wearable power sources. The kit could also be for just a left foot, or just a right foot, in which case only one pad is included, one sock support system, and one wearable power source.

These kits may also contain additional elements, including a user manual, drugs/active agents, a conductive gel, petroleum jelly, water or other liquids.

According to one embodiment, the iontophoresis device, or any of its subsystems, may be built into devices, tools, systems, that are used daily, weekly, monthly, frequently or infrequently by users, for example into a steering wheel, winter gloves, a mug, a computer mouse, a touchpad, or a tooth brush.

Beyond the applications for management of hidrosis and treatment of hyperhidrosis, the devices for delivery of electrical current to the body described in this application may also be used for a number of other applications, including transdermal drug delivery to a pre-selected current delivery area, treatment of inflammation, pain, wounds, infection, edema, scar tissue and adhesions, myopathy, cancer, skin discoloration, fungal infections, athlete's foot, resolution of soft-tissue mineralization, diagnosis of cystic fibrosis.

In one embodiment, the invention provides a method of delivering electrical current to an area of skin, the method comprising: adhering two or more adhesive electrode assemblies to a treatment area; optionally applying a support system over said electrode assemblies; electrically connecting said electrode assemblies to a wearable power source through an electrical connection system; and providing a dose of electrical current to said skin. The electrode assemblies are preferably pads comprising one or more tabs on pad edges, a conductive layer and an adhesive hydrogel. The support system improves the connection between the electrode assembly or assemblies and the skin. The method may also comprise periodically reversing a polarity of current delivered to the electrode assemblies. The electrical current may be direct or pulsed current with a direct current offset. In one implementation, the electrode assemblies together form a hand-shape or sole-shape. The controller circuit may comprise instructions to automatically limit a density of the electrical current below a selectable, pre-determined threshold. The support system may be selected from the group consisting of gloves, sleeves, socks, face masks, shirts, and belts.

Iontophoresis Device: Example of Use 1—Palmar Hyperhidrosis

A user uses an iontophoresis device, illustrated in FIG. 27. The user takes a first hand-shaped electrode assembly pad 322 of its bottom liner and adheres it to one hand by positioning the hand on the pad according to the instructions for use. The user takes the second hand-shaped electrode assembly pad 324 of its bottom liner and adheres it to the other hand by positioning the hand on the pad according to the instructions for use. The user connects both pads with the connector cables 326, 328 and to the power source 330. The current circuit is completed by the body 332. The user selects the desired current intensity, for example 20 mA, and starts the treatment. Electrical current will be delivered for the required treatment time, for example 30 min. Once finished, the user disconnects the power source and connector cable from the hand-shaped electrode assembly pads 322, 324. The user removes the first hand-shaped electrode assembly pad 322 from one hand, and places it back on its bottom liner or disposes of it. The user removes the second hand-shaped electrode assembly pad 324 from the other hand, and places it back on its bottom liner or disposes of it.

Iontophoresis Device: Example of Use 2—Palmar Hyperhidrosis

A user uses an iontophoresis device, illustrated in FIG. 28. The user takes a pad (that contains both anodal 334 and cathodal 336 segments) of its bottom liner and adheres it to one hand 338 by positioning the hand on the pad according to the instructions for use. The user connects the pad with a wearable power source 340 using connectors 342, 344. The user takes the second pad (that contains both anodal and cathodal segments) of its bottom liner and adheres it to the other hand by positioning the hand on the pad according to the instructions for use. The user connects the pad with a wearable power source. The user selects the desired current intensity, for example 10 mA, and starts the treatment. Electrical current will be delivered for the required treatment time, for example 30 min. Once finished, the user disconnects each wearable power source from its pad. The user removes the first pad from one hand, and places it back on its bottom liner or disposes of it. The user removes the second pad from the other hand, and places it back on its bottom liner or disposes of it. Note that example of use 2 uses a lower current intensity compared to the current intensity used in example of use 1 if used for users with the same hand size, while the user may still receive about the same current density given the difference in surface area of the electrode assemblies.

Iontophoresis Device: Example of Use 3—Palmar Hyperhidrosis

A user takes a pad (that contains both anodal and cathodal segments) of its bottom liner and adheres it to one hand by positioning the hand on the pad according to the instructions for use. The user slides this hand into a glove support system, as illustrated in FIG. 22, and connects the system with a first wearable power source. The user takes the second pad (that contains both anodal and cathodal segments) of its bottom liner and adheres it to the other hand by positioning the hand on the pad according to the instructions for use. The user slides this hand into a second glove support system, as illustrated in FIG. 22, and connects the system with a second wearable power source. The user selects the desired current intensity, for example 10 mA, and starts the treatment. Electrical current will be delivered for the required treatment time, for example 30 min. Once finished, the user disconnects each wearable power source and takes of the glove support systems. The user removes the first pad from one hand, and places it back on its bottom liner or disposes of it. The user removes the second pad from the other hand, and places it back on its bottom liner or disposes of it.

Iontophoresis Device: Example of Use 4—Drug Delivery

A user takes a pad (that contains both anodal and cathodal segments) of its bottom liner and applies a drug to a marked area of the pad. The user adheres the pad to one hand by positioning the hand on the pad according to the instructions for use. The user connects the pad with a wearable power source. The user selects the desired current intensity, for example 8 mA, and starts the treatment. Electrical current will be delivered for the required treatment time, for example 30 min. Once finished, the user disconnects the wearable power source from the pad. The user removes the pad from the hand, and places the pad back on its bottom liner or disposes of it.

Iontophoresis Device: Example of Use 5—Palmar and Plantar Hyperhidrosis

A user takes a hand-shaped electrode assembly pad of its bottom liner and adheres it to one hand by positioning the hand on the pad according to the instructions for use. The user takes a sole-shaped electrode assembly pad of its bottom liner and adheres it to a foot by positioning the foot on the pad according to the instructions for use. The user connects both pads with the connector cable and to the power source. The user selects the desired current intensity, for example 20 mA, and starts the treatment. Electrical current will be delivered for the required treatment time, for example 30 min. Once finished, the user disconnects the power source and connector cable from the hand-shaped and sole-shaped electrode assembly pads. The user removes the hand-shaped electrode assembly pad from the hand, and places it back on its bottom liner or disposes of it. The user removes the sole-shaped electrode assembly pad from the foot, and places it back on its bottom liner or disposes of it.

Iontophoresis Device: Example of Use 6—Plantar Hyperhidrosis

A user takes a pad (that contains both anodal and cathodal segments) of its liner and adheres it to one foot by positioning the foot on the pad according to the instructions for use. The user slides this foot into a sock support system and connects the system with a first wearable power source. The user takes the second pad (that contains both anodal and cathodal segments) of its liner and adheres it to the other foot by positioning the foot on the pad according to the instructions for use. The user slides this foot into a second sock support system, and connects the system with a second wearable power source. The user selects the desired current intensity, for example 10 mA, and starts the treatment. Electrical current will be delivered for the required treatment time, for example 30 min. Once finished, the user disconnects each wearable power source and takes of the sock support systems. The user removes the first pad from one foot, and places it back on its liner or disposes of it. The user removes the second pad from the other foot, and places it back on its liner or disposes of it.

The invention claimed is:

1. An iontophoresis device configured to deliver electrical current to a user's hand, the device comprising:
   an insulation layer;
   a first electrode assembly set carried by the insulation layer and comprising one or more electrode assemblies, wherein the first electrode assembly set comprises a finger- or thumb-shaped protrusion;
   a first electrical connection system electrically connected to the first electrode assembly set;
   a second electrode assembly set carried by the insulation layer and comprising one or more electrode assemblies, the second electrode assembly set laterally separated from the first electrode assembly set along the insulation layer;
   a second electrical connection system electrically connected to the second electrode assembly set; and
   a wearable power generator having a positive terminal electrically coupled to the first electrical connection system and a negative terminal electrically coupled to the second electrical connection system,
   wherein, when the device is applied to the user's hand, the first electrode assembly set is positioned substantially distal to the second electrode assembly set and is positioned between the insulation layer and the hand.

2. The device of claim 1, wherein the first electrode assembly set comprises four finger-shaped protrusions and a thumb-shaped protrusion.

3. The device of claim 1, wherein the second electrode assembly set comprises a palm portion and a thumb-shaped protrusion.

4. The device of claim 1, wherein the insulation layer is substantially hand-shaped.

5. The device of claim 1, further comprising a controller circuit in electrical communication with the wearable power generator, the controller circuit configured to limit a density of electrical current delivered to the first electrode assembly set and the second electrode assembly set below a selectable pre-determined threshold.

6. The device of claim 5, wherein the controller circuit is adapted to deliver alternating electrical current to the first electrical connection system and the second electrical connection system.

7. The device of claim 1, wherein the wearable power generator is battery powered.

8. The device of claim 1, further comprising a glove surrounding the first electrode assembly set and the second electrode assembly set.

9. The device of claim 8, wherein the glove comprises a support system configured to apply pressure to the first electrode assembly set and/or the second electrode assembly set to promote contact between electrode assemblies of the first electrode assembly set and/or electrode assemblies of the second electrode assembly set and the hand of the user while wearing the glove.

10. The device of claim 8, wherein the glove is a compressive glove configured to promote contact between electrode assemblies of the first electrode assembly set and the hand of the user while wearing the glove.

* * * * *